US011766301B2

(12) United States Patent
Diolaiti et al.

(10) Patent No.: US 11,766,301 B2
(45) Date of Patent: Sep. 26, 2023

(54) TECHNIQUES FOR CONTROLLING A MOVEABLE COMPONENT

(71) Applicant: INTUITIVE SURGICAL OPERATIONS, INC., Sunnyvale, CA (US)

(72) Inventors: Nicola Diolaiti, Menlo Park, CA (US); Jeffrey D. Brown, Palo Alto, CA (US); Daniel H. Gomez, Los Gatos, CA (US); Robert E. Holop, Santa Clara, CA (US); Anthony K. McGrogan, San Jose, CA (US); Probal Mitra, Sunnyvale, CA (US); Craig R. Ramstad, Minden, NV (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 197 days.

(21) Appl. No.: 17/236,868

(22) Filed: Apr. 21, 2021

(65) Prior Publication Data
US 2021/0236220 A1 Aug. 5, 2021

Related U.S. Application Data

(63) Continuation of application No. 16/317,334, filed as application No. PCT/US2017/032930 on May 16, 2017, now Pat. No. 11,020,191.
(Continued)

(51) Int. Cl.
*A61B 34/32* (2016.01)
*A61B 34/37* (2016.01)
(Continued)

(52) U.S. Cl.
CPC .............. *A61B 34/32* (2016.02); *A61B 34/37* (2016.02); *A61B 34/74* (2016.02); *A61B 46/10* (2016.02); *B25J 9/0009* (2013.01)

(58) Field of Classification Search
CPC ......... A61B 34/32; A61B 34/37; A61B 34/74; A61B 46/10; A61B 2017/00017;
(Continued)

(56) References Cited

U.S. PATENT DOCUMENTS 6,671,581 B2  12/2003  Niemeyer et al.
6,963,792 B1  11/2005  Green
(Continued)

FOREIGN PATENT DOCUMENTS

JP  2014076204 A  5/2014
KR   100640019 B1  10/2006
(Continued)

OTHER PUBLICATIONS

Extended European Search Report for Application No. EP17828112.7 dated Jan. 28, 2020, 10 pages.
(Continued)

*Primary Examiner* — Jonathan T Kuo
(74) *Attorney, Agent, or Firm* — Artegis Law Group, LLP

(57) ABSTRACT

Techniques for controlling a moveable component include a system, a method, and/or a non-transitory computer-readable medium. A controller coupled to the moveable component is configured to hold the moveable component at a first position, detect a disturbance that moves the moveable component from the first position, in response to a detection of the disturbance, move the moveable component according to a first motion, continue to move the moveable component according to the first motion until a stop condition is detected, even if the disturbance ends before the stop condition is detected, and in response to a detection of the
(Continued)

stop condition, hold the moveable component at a second position.

20 Claims, 17 Drawing Sheets

Related U.S. Application Data

(60) Provisional application No. 62/362,192, filed on Jul. 14, 2016.

(51) Int. Cl.
*A61B 34/00* (2016.01)
*A61B 46/10* (2016.01)
*B25J 9/00* (2006.01)

(58) Field of Classification Search
CPC ... A61B 2090/064; A61B 34/30; A61B 34/70; A61B 34/00; A61B 2017/00477; A61B 34/35; B25J 9/0009
See application file for complete search history.

(56) References Cited

U.S. PATENT DOCUMENTS

| | | | |
|---|---|---|---|
| 7,152,456 B2 * | 12/2006 | Eaton | G01B 5/004 73/1.79 |
| 7,725,214 B2 | 5/2010 | Diolaiti | |
| 8,918,211 B2 | 12/2014 | Diolaiti et al. | |
| 9,060,678 B2 | 6/2015 | Larkin et al. | |
| 9,283,048 B2 | 3/2016 | Kostrzewski et al. | |
| 10,579,045 B2 * | 3/2020 | Gombert | B25J 9/1656 |
| 11,020,191 B2 | 6/2021 | Diolaiti et al. | |
| 2005/0150123 A1 * | 7/2005 | Eaton | G01B 5/004 33/503 |
| 2011/0277775 A1 | 11/2011 | Holop et al. | |
| 2011/0277776 A1 | 11/2011 | McGrogan et al. | |
| 2013/0096575 A1 | 4/2013 | Olson et al. | |
| 2014/0052154 A1 | 2/2014 | Griffiths et al. | |
| 2014/0130810 A1 | 5/2014 | Azizian et al. | |
| 2015/0047647 A1 | 2/2015 | Winer et al. | |
| 2016/0184032 A1 * | 6/2016 | Romo | B25J 9/1694 901/46 |
| 2016/0184037 A1 | 6/2016 | Cooper et al. | |
| 2017/0160721 A1 * | 6/2017 | Gombert | B25J 13/025 |
| 2017/0252921 A1 | 9/2017 | Hynna et al. | |
| 2018/0200014 A1 | 7/2018 | Bonny et al. | |

FOREIGN PATENT DOCUMENTS

| | | |
|---|---|---|
| KR | 101667032 B1 | 10/2016 |
| WO | WO-2015142955 A1 | 9/2015 |
| WO | WO-2017015207 A1 | 1/2017 |
| WO | WO-2018013236 A1 | 1/2018 |

OTHER PUBLICATIONS

International Search Report and Written Opinion for Application No. PCT/US2017/032930, dated Aug. 18, 2017, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

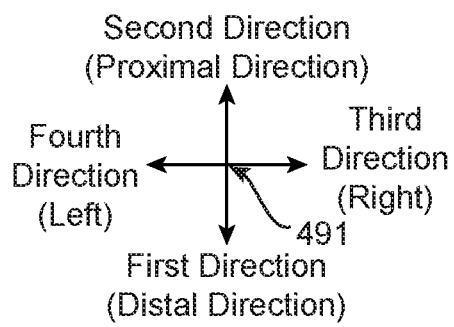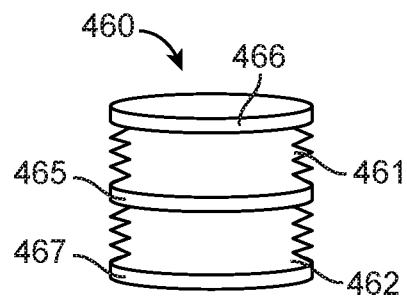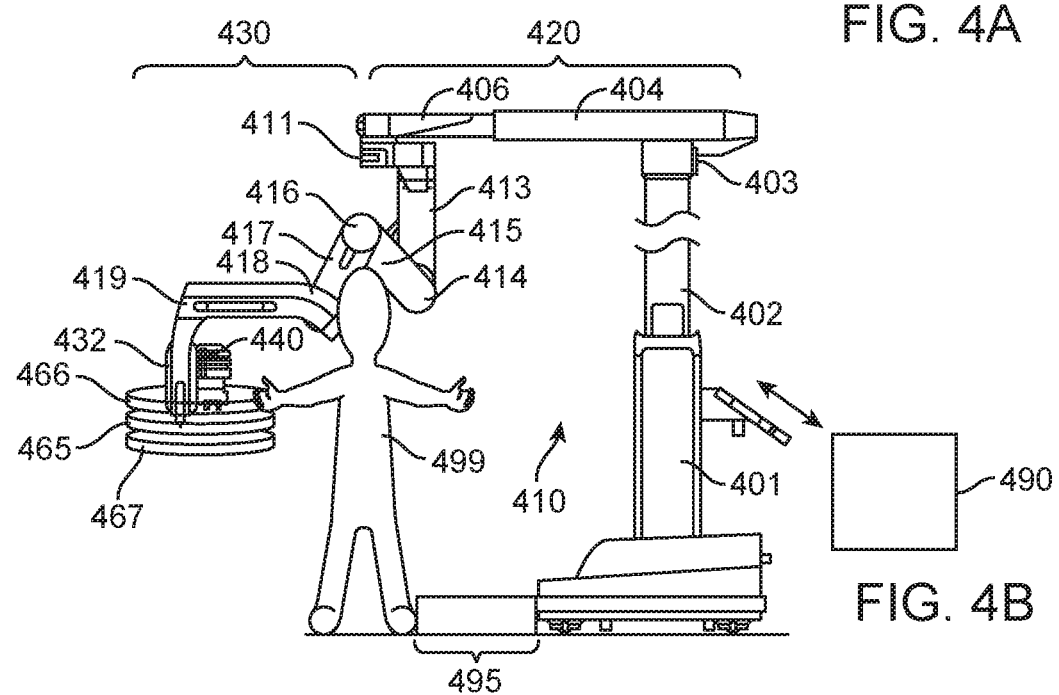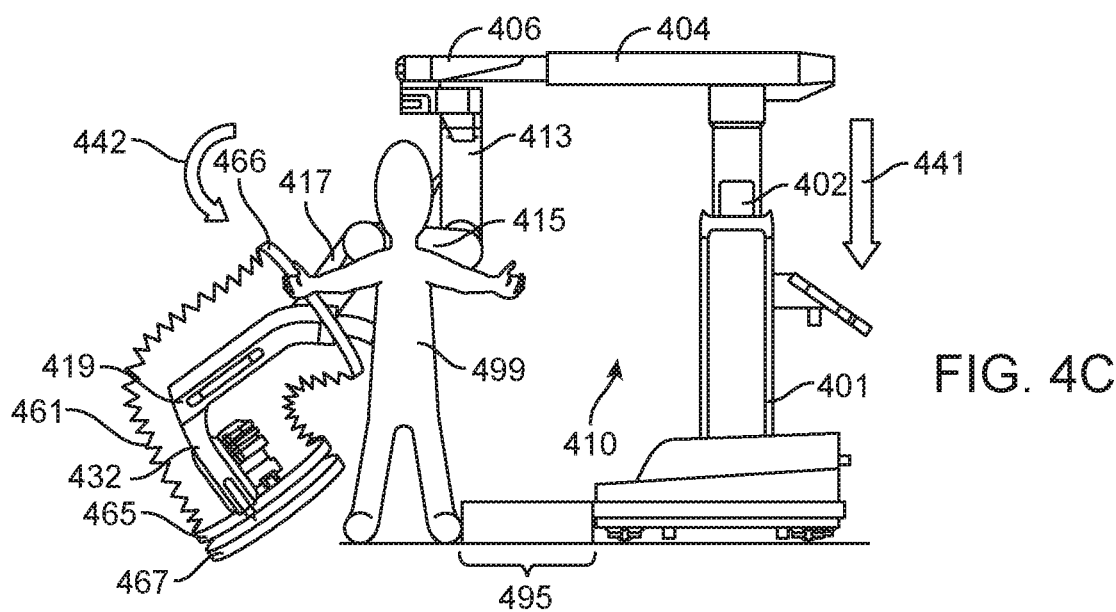

TECHNIQUES FOR CONTROLLING A MOVEABLE COMPONENT

RELATED APPLICATION

This patent application is a continuation of U.S. patent application Ser. No. 16/317,334 filed on Jan. 11, 2019, which is a U.S. National Stage patent application of International Patent Application No. PCT/US2017/032930 filed on May 16, 2017, the benefit of which is claimed, and claims priority to and the benefit of the filing date of U.S. Provisional Patent Application 62/362,192, entitled "AUTOMATIC MANIPULATOR ASSEMBLY DEPLOYMENT FOR DRAPING" filed Jul. 14, 2016, each of which is incorporated by reference herein in its entirety.

TECHNICAL FIELD

The present invention relates generally to draping surgical systems, and more particularly to automation that assists in the draping of a surgical system.

BACKGROUND

A surgical drape has been previously used to cover a surgical manipulator such as plurality of surgical instrument manipulator assemblies 140 in computer-assisted surgical system 100. The drapes have taken various forms. In each instance, the manipulator and associated supports links are manually covered with a surgical drape prior to the start of the surgical procedure.

Surgical system 100 is a computer-assisted surgical system that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Pat. No. 9,060,678 B2, which is incorporated by reference herein.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 194 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Base 101 of patient side support system 110 supports an arm assembly that includes a passive, uncontrolled setup arm assembly 120 and an actively controlled manipulator arm assembly 130. Actively controlled manipulator arm assembly 130 is referred to as entry guide manipulator 130.

In one example, setup arm assembly 120 includes two passive rotational setup joints 103 and 105. Rotational setup joints 103 and 105 allow manual positioning of coupled setup links 104 and 106 if the joint brakes for setup joints 103 and 105 are released. Alternatively, some of these setup joints may be actively controlled, and more or fewer setup joints may be used in various configurations. Setup joints 103 and 105 and setup links 104 and 106 allow a person to place entry guide manipulator 130 at various positions and orientations in Cartesian x, y, and z space. A prismatic setup joint (not shown) between setup link 104 of setup arm assembly 120 and base 101 may be used for vertical adjustments 112.

A remote center of motion 146 is a location at which yaw, pitch, and roll axes intersect (i.e., the location at which the kinematic chain remains effectively stationary while joints move through their range of motion). Some of these actively controlled joints are manipulators that are associated with controlling DOFs of individual instruments, and others of these actively controlled joints are associated with controlling DOFs of a single assembly of these manipulators. The active joints and links are movable by motors or other actuators and receive movement control signals that are associated with master arm movements at surgeon's console 194.

As shown in FIG. 1, a manipulator assembly yaw joint 111 is coupled between an end of setup link 106 and a first end, e.g., a proximal end, of a first manipulator link 113. Yaw joint 111 allows first manipulator link 113 to move with reference to setup link 106 in a motion that may be arbitrarily defined as "yaw" around a manipulator assembly yaw axis 123. As shown, the rotational axis of yaw joint 111 is aligned with remote center of motion 146, which is generally the position at which an instrument enters the patient (e.g., at the umbilicus for abdominal surgery).

In one embodiment, setup link 106 is rotatable in a horizontal or x, y plane and yaw joint 111 is configured to allow first manipulator link 113 in entry guide manipulator 130 to rotate about yaw axis 123. Setup link 106, yaw joint 111, and first manipulator link 113 provide a constantly vertical yaw axis 123 for entry guide manipulator 130, as illustrated by the vertical line through yaw joint 111 to remote center of motion 146.

A distal end of first manipulator link 113 is coupled to a proximal end of a second manipulator link 115 by a first actively controlled rotational joint 114. A distal end of second manipulator link 115 is coupled to a proximal end of a third manipulator link 117 by a second actively controlled rotational joint 116. A distal end of third manipulator link 117 is coupled to a distal portion of a fourth manipulator link 119 by a third actively controlled rotational joint 118.

In one embodiment, links 115, 117, and 119 are coupled together to act as a coupled motion mechanism. Coupled motion mechanisms are well known (e.g., such mechanisms are known as parallel motion linkages when input and output link motions are kept parallel to each other). For example, if rotational joint 114 is actively rotated, joints 116 and 118 are also actively rotated so that link 119 moves with a constant relationship to link 115. Therefore, it can be seen that the rotational axes of joints 114, 116, and 118 are parallel. When these axes are perpendicular to rotational axis 123 of yaw joint 111, links 115, 117, and 119 move with reference to link 113 in a motion that may be arbitrarily defined as "pitch" around a manipulator assembly pitch axis.

The manipulator pitch axis extends into and out of the page in FIG. 1 at remote center of motion 146, in this aspect. The motion around the manipulator assembly pitch axis is represented by arrow 121. Since links 115, 117, and 119 move as a single assembly, first manipulator link 113 may be considered an active proximal manipulator link, and second through fourth manipulator links 115, 117, and 119 may be considered collectively an active distal manipulator link.

An entry guide manipulator assembly platform 132, sometimes referred to as platform 132, is coupled to a distal end of fourth manipulator link 119. An entry guide manipulator assembly 133 is rotatably mounted on platform 132. Entry guide manipulator assembly 133 includes an instrument manipulator positioning system.

Entry guide manipulator assembly 133 rotates plurality of surgical instrument manipulator assemblies 140 as a group around axis 125. Specifically, entry guide manipulator assembly 133 rotates as a single unit with reference to platform 132 in a motion that may be arbitrarily defined as "roll" around an entry guide manipulator assembly roll axis 125.

Each of a plurality of surgical instrument manipulator assemblies 140 is coupled to entry guide manipulator assembly 133 by a different insertion assembly 135 (also called "insertion mechanism 135"). In one aspect, each insertion assembly 135 is a telescoping assembly that moves the corresponding surgical instrument manipulator assembly away from and towards entry guide manipulator assembly 133. In FIG. 1, each of the insertion assemblies is in a fully retracted position.

Each of the plurality of surgical instrument manipulator assemblies includes a plurality of motors that drive a plurality of outputs in an output interface of that instrument manipulator assembly. See U.S. Patent Application Publication No. US 2016/0184037 A1, which is incorporated by reference, for one example of an instrument manipulator assembly and a surgical instrument that can be coupled to the instrument manipulator assembly.

In one aspect, a membrane interface that is part of a surgical drape may be placed between the instrument mount interface of a surgical instrument manipulator assembly and the input interface of the transmission unit of a corresponding surgical instrument. See, for example, U.S. Patent Application Publication No. US 2011/0277776 A1 for an example of the membrane interface and surgical drape. In another aspect, a sterile adapter that is part of a surgical drape may be placed between the instrument mount interface of the surgical instrument manipulator assembly and the input interface of the transmission unit of the corresponding surgical instrument. See, for example, U.S. Patent Application Publication No. US 2011/0277775 A1 for an example of a sterile adapter and a surgical drape.

FIG. 2 is a perspective view of a drape portion 200 of an extended surgical drape including a sterile adapter 250. Drape portion 200 includes a plurality of drape sleeves 205 coupled between rotatable seal 208 and sterile adapter 250.

Rotatable seal 208 operably couples proximal openings 203 of plurality of drape sleeves 205 to the manipulator platform of the manipulator arm assembly. In one example, rotatable seal 208 includes a rotatable labyrinth seal having a roll cover portion 208a and a base comb portion 208b. Base comb portion 208b is rotatable relative to roll cover portion 208a. Base comb portion 208b includes a disc with ribs 204 that form a plurality of wedge-shaped "frames" with apertures, each of the frames is sized to circumscribe a surgical instrument manipulator assembly. A proximal end of each of plurality of drape sleeves 205 is coupled to a different one of the plurality of wedge-shaped frames of base comb portion 208b. Ribbed base comb portion 208b aids in draping each individual one of the surgical instrument manipulator assemblies, which are closely clustered on the rotatable base plate of entry guide manipulator assembly 133, and further aids in maintaining the orientation and arrangement of each of plurality of drape sleeves 205 as the draped surgical instrument manipulator assemblies move during a surgical procedure.

FIG. 2 illustrates each of plurality of drape sleeves 205 in an extended state. Each of plurality of drape sleeves 205 may independently retract and extend as a corresponding surgical instrument manipulator assembly is independently and/or dependently controlled with respect to other surgical instrument manipulator assemblies.

Roll cover portion 208a fixedly mounts to frame of manipulator platform 132 (e.g., the manipulator halo) and base comb portion 208b fixedly mounts to the rotatable base plate of entry guide manipulator assembly 133, such that when the rotatable base plate of entry guide manipulator assembly 133 is rotated, base comb portion 208b also rotates in combination with the draped surgical instrument manipulator assemblies. Since the proximal end of each of plurality of drape sleeves 205 is coupled to base comb portion 208b, all the drape sleeves 205 rotate together as a group with reference to a more proximal drape portion 210.

SUMMARY

A controller in a computer-assisted teleoperated surgical system, upon detecting a position change indication, automatically moves a part of the system to facilitate draping of that part with a sterile surgical drape, sometimes referred to as a surgical drape. This speeds the draping process and diminishes the likelihood that the sterile surgical drape is damaged or contaminated during the draping of that part of the system compared to a user manually draping that part.

In one aspect, the part has a first position. The controller is coupled to the part, and the controller is configured to detect a position change indication of the part. Also, the controller is configured to automatically move the part to a second position to facilitate draping of a surgical apparatus portion of the surgical system. The first position is different from the second position, and the controller automatically moves the part in response to detection, by the controller, of the position change indication.

In one aspect, the position change indication is a position tracking disturbance created by the user tapping on the part. However, in other aspects, the position change indication is a signal from a motion control input device on the part that indicates a direction to move the part. This signal is generated by a user interaction with the motion control input device.

In one aspect, the part is a manipulator component and the computer-assisted teleoperated surgical system includes a surgical drape. In this aspect, the controller is configured to automatically move the manipulator component to a second position to facilitate draping of a surgical apparatus portion of the surgical system. This includes the controller being configured to automatically move the manipulator component into a portion of the surgical drape.

In another aspect, the part is a manipulator component and the computer-assisted teleoperated surgical system includes a surgical drape, and the controller is configured to automatically move the manipulator component to a second position to facilitate draping of a surgical apparatus portion of the surgical system. This includes the controller being configured to automatically move the manipulator component within a portion of the surgical drape. In one aspect, the portion of the surgical drape is a drape sleeve.

In one aspect, the part is a link, and in another aspect the part is a manipulator assembly. For example, the link can be a link in an entry guide manipulator, while the manipulator assembly can be a surgical instrument manipulator assembly. These examples are not intended to be inclusive. Sometimes the part is characterized as a manipulator component.

In one aspect, the controller being configured to detect a position change indication of the part includes the controller being configured to detect a position tracking disturbance. The position tracking disturbance is created by a user input on the part. In one aspect, the user input on the part is the user tapping the part.

In one aspect, the controller includes a state machine. The state machine includes a position hold state and an advance state. The state machine transitions from the positon hold state to the advance state if a position error in the position of the part occurs for at least a predetermined time interval. In the advance state, the controller moves the part, for example, the part drifts in the direction of a user's tap, such as toward or away from the source of the tap.

In one aspect, the controller further includes a drift control loop. The drift control loop is a control loop configured in the controller so that the controlled part moves with constant speed and with reduced torque limits so that obstacles or user tapping of the controlled part are detected by a position tracking disturbance exceeding set limits. In one aspect, the drift control loop is implemented as a feedback proportional differential controller with cascaded saturations.

A method of draping a part of a patient side support system includes detecting, by a controller coupled to the patient side support system, a position change indication of the part, and automatically moving, by the controller, the part from a first position to a second position to facilitate draping of the patient side support system. The second position is different from the first position, and the automatic movement by the controller is in response to detection, by the controller, of the position change indication of the part.

In one aspect of this method, the position change indication is a position tracking disturbance created by the user tapping on the part. However, in other aspects, the position change indication is a signal from a motion control input device on the part that indicates a direction to move the part. This signal is generated by a user interaction with the motion control input device on the part.

In one aspect of this method, the part is a link, and in another aspect the part is a manipulator assembly. For example, the link can be a link in an entry guide manipulator, while the manipulator assembly can be a surgical instrument manipulator assembly. These examples are not intended to be inclusive. Sometimes the part is characterized as a manipulator component.

In one aspect, the method further includes determining, by the controller, mounting of a sterile surgical drape on the patient side support system. Also, the detecting, by the controller, a position change indication of the part includes detecting a position tracking disturbance of the part, where the position tracking disturbance is created by a user input on the part. In one aspect, the method includes receiving, by the controller, the user input. In one the aspect, the user input on the part includes a user tapping the part, and in another aspect, the user input on the part includes a user interacting with a motion control input component on the part.

In still a further aspect, the detecting, by the controller, a position tracking disturbance includes determining, by the controller, a position of the part of the patient side support system and determining, by the controller, whether the position of the part of the patient side support system has changed.

In one aspect, if the controller determines that the position of the part of the patient side support system has changed, the controller also determines whether the position of the part of the patient side support system has changed for a predetermined time interval. In this aspect, the automatic movement is performed if the controller determines that the position of the part of the patient side support system has changed and that the position of the part of the patient side support system has changed for the predetermined time interval. The controller also determines whether movement of the part of the patient side support system is stopped. The controller commands the part of the patient side support system to maintain a latched position if the controller finds that movement of the part of the patient side support system is stopped. In one aspect, the movement must be stopped for a predetermined time interval before the controller commands the part of the patient side support system to maintain the latched position.

In a further aspect, a non-transitory tangible computer-readable medium storing instructions for controlling the operation of one or more hardware processors to perform a method includes detecting a position change indication of a part of a patient side support system, the part having a first position, and automatically moving the part to a second position to facilitate draping of the patient side support system, the second position being different from the first position, and the automatically moving being in response to detection of the position change indication of the part.

BRIEF DESCRIPTION OF THE DRAWINGS

FIG. 4A is an illustration of a sterile surgical drape assembly.

FIGS. 4B to 4G illustrate the automatic draping of links of a surgical instrument manipulator assembly by automatically moving each of the links into a portion of the sterile surgical drape assembly of FIG. 4A.

Figure 1:
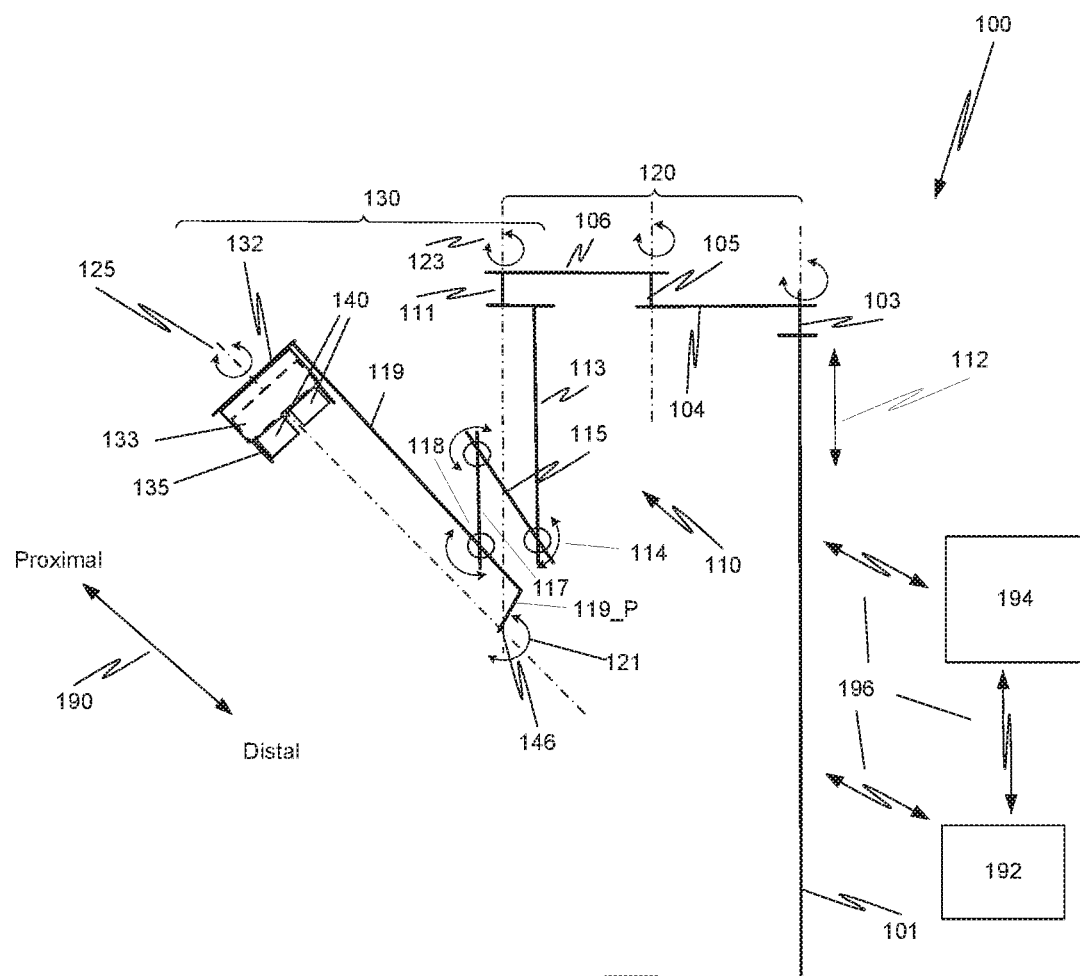
FIG. 1 is an illustration of a prior art computer-assisted teleoperated surgical system.
Figure 2:
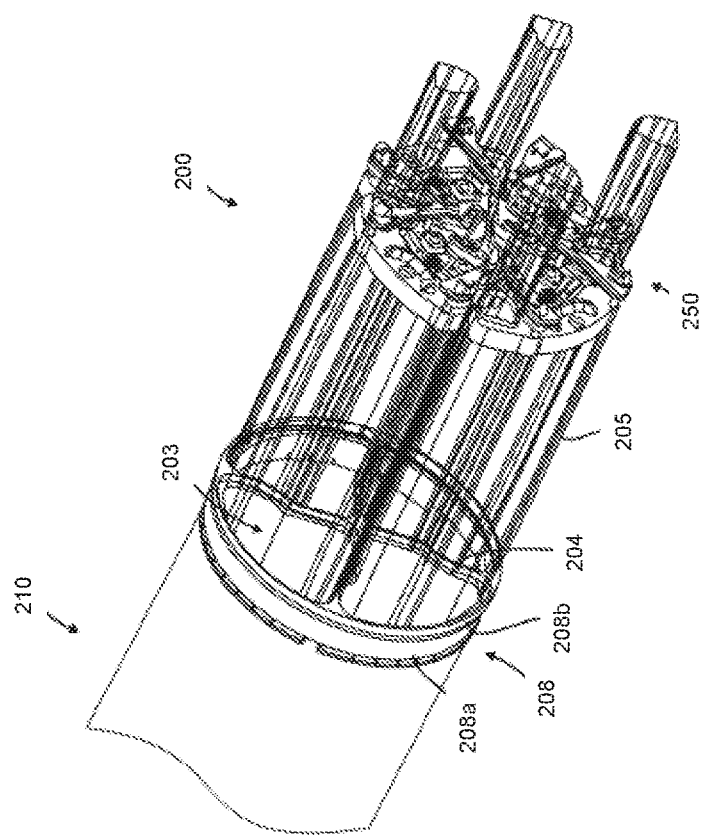
FIG. 2 is an illustration of a prior art sterile surgical drape mounted on a portion of the surgical system of FIG. 1.

In the drawings, for single digit figure numbers, the first digit in the reference numeral of an element is the number of the figure in which that element first appears. For double-digit figure numbers, the first two digits in the reference numeral of an element is the number of the figure in which that element first appears.

DETAILED DESCRIPTION

In one aspect, a controller 390 in a computer-assisted teleoperated surgical system automatically moves a part of the system into a portion of a sterile surgical drape to facilitate draping of that part. This speeds the draping process and diminishes the likelihood that the sterile surgical drape is damaged or contaminated during the draping of that part of the system compared to the user manually draping that part.

Figure 3A:
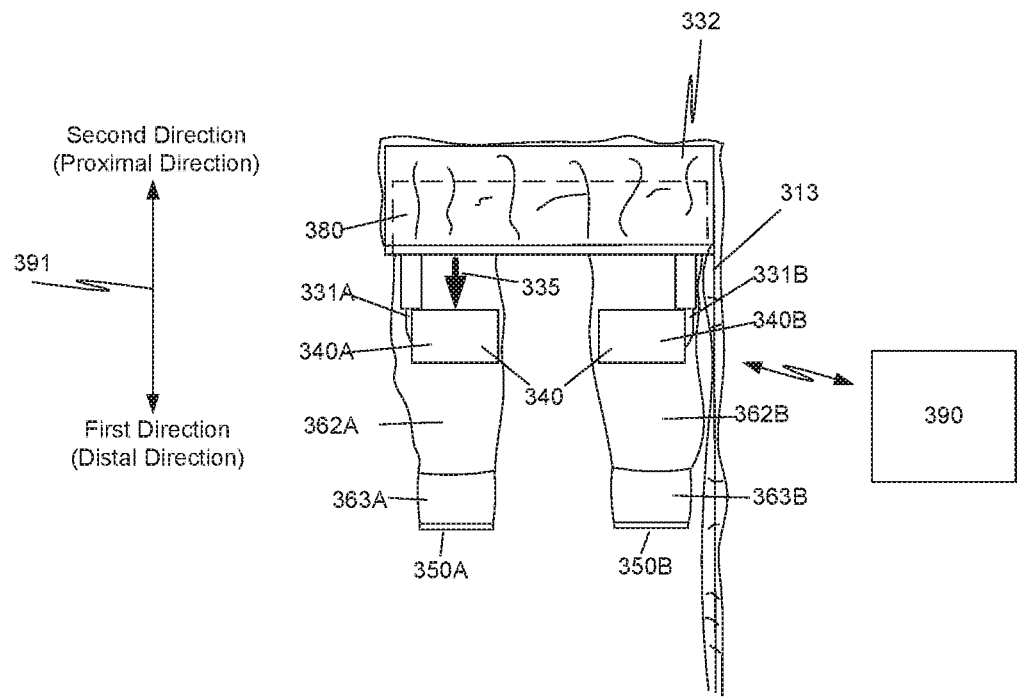
FIGS. 3A and 3B illustrate the automatic drift of a surgical instrument manipulator assembly into a sleeve of a sterile surgical drape.

For example, in FIG. 3A, a portion of a patient side support system is illustrated. The patient side support system may also be termed a "patient side cart," when the patient side support system is configured as a cart. In particular, a platform 332 is coupled to one end of a link 313 of an entry guide manipulator. The entry guide manipulator's structure is similar to the structure of entry guide manipulator 130. An entry guide manipulator assembly 380 is mounted in platform 332. Controller 390 is interconnected to the patient side support system that includes these components by wired (electrical or optical) or wireless connections.

Each surgical instrument manipulator assembly 340A, 340B of a plurality of surgical instrument manipulator assemblies 340 is connected to entry guide manipulator assembly 380 by an insertion assembly 331A, 331B. Entry guide manipulator assembly 380 rolls plurality of surgical instrument manipulator assemblies 340 as a group. For draping, entry guide manipulator assembly 380 also moves each of plurality of surgical instrument manipulator assemblies 340 as far apart as possible.

In FIG. 3A, the links of the entry guide manipulator have been draped. Each drape sleeve 362A, 362B of a plurality of drape sleeves of a sterile surgical drape is extended in a distal direction. Each drape sleeve 362A, 362B surrounds a corresponding insertion assembly 331A, 331B, and a surgical instrument manipulator assembly 340A, 340B.

In this example, at the distal end of each drape sleeve 362A, 362B is a boot 363A, 363B and a sterile adapter assembly 350A, 350B. Each sterile adapter assembly 350A, 350B mounts in a distal face of the corresponding surgical instrument manipulator assembly 340A, 340B. Sterile adapter assemblies 350A, 350B are each an example of a structure that includes a mechanical interface between a drive interface of a drive system of a surgical instrument manipulator assembly and a driven interface of a surgical instrument.

To position surgical instrument manipulator assembly 340A closer to sterile adapter assembly 350A to facilitate mounting sterile adapter assembly 350A without contaminating or damaging sterile surgical drape sleeve 362A, a user taps, e.g., pushes, surgical instrument manipulator assembly 340A in a distal direction, as represented by arrow 335. It should be understood that when a user taps on a part of patient side support system 310, such as surgical instrument manipulator assembly 340A, the user applies a force on the component in a particular direction for a particular amount of time, which in turn results in a displacement of the component. The displacement creates an error in the position of that component relative to the position where controller 390 expects the component to be. (Herein, arrow 391 defines the distal and proximal directions, which are examples of first and second directions, respectively.)

Controller 390, which knows the position and velocity of surgical instrument manipulator assembly 340A, detects a position tracking disturbance of surgical instrument manipulator assembly 340A, which is caused by the user tapping surgical instrument manipulator assembly 340A. In this aspect, controller 390 is configured to automatically move surgical instrument manipulator assembly 340A within the surgical drape when the position tracking disturbance satisfies a criterion or set of criteria. As examples, various aspects automatically move surgical instrument manipulator assembly 340A within the surgical drape in response to the position tracking disturbance exceeding a specified threshold (such as may be associated with user force above a particular magnitude), changes from below a specified threshold to above the specified threshold to back below the threshold (such as may be associated with the noncontact-contact-noncontact events of a tap), changes in a way that indicate tapping in a particular direction, changing between below and above a specified threshold a specified number of times (indicating a single tap, double tap, or a greater number of taps), meeting time requirements associated with particular types of tapping (such as a long tap or short tap between associated lower and/or higher time bounds), and/or some other criteria for tapping magnitudes, directions, durations, etc. Aspects for determining the specified threshold are described more completely below.

Thus, in response to the position tracking disturbance, controller 390 moves surgical instrument manipulator assembly 340A in the distal direction, e.g., surgical instrument manipulator assembly 340A drifts in the distal direction. For example, controller 390 commands a motor in insertion assembly 331A to move insertion assembly 331A so that surgical instrument manipulator assembly 340A is moved in the distal direction. In general, when it is stated herein that a controller moves a part or controls a part, it should be understood that the controller issues one or more commands to a device, e.g., a motor, or devices that in turn act on the part in response to the one or more commands.

The motion of surgical instrument manipulator assembly 340A continues in the distal direction until the user taps surgical instrument manipulator assembly 340A in the proximal direction, as indicated by arrow 336, or until surgical instrument manipulator assembly 340A contacts an impediment that slows its motion in the distal direction, or until surgical instrument manipulator assembly reaches a predetermined position, e.g., a maximum distance from a home position or other known position, which is permitted during draping. If surgical instrument manipulator assembly 340A is stopped in other than the predetermined position, subsequent taps on surgical instrument manipulator assembly 340A by the user cause surgical instrument manipulator assembly 340A to move in the direction of each of the taps.

The automatic movement of surgical instrument manipulator assembly in response to a tap by a user speeds up the draping process and reduces the likelihood of damaging or contaminating the sterile surgical drape. In system 100 with sterile surgical drape comprising drape portion 200, a surgical instrument manipulator assembly could be manually moved in the distal direction by the user grasping a clutch button on the surgical instrument manipulator assembly and then moving the surgical instrument manipulator assembly along the insertion assembly.

Thus, to mount a sterile adapter assembly, a user would have to grasp the drape sleeve distal to the clutch button, fold the drape sleeve proximal to the point grasped, move the folded drape sleeve up and over the surgical instrument manipulator assembly until the user could grasp the clutch button, and then manually move the surgical instrument manipulator distally until the folded portion was unfolded. This was repeated until the surgical instrument manipulator assembly was in the position shown in FIG. 3B.

The folding of the drape sleeve up and around the surgical instrument manipulator risked catching the drape sleeve on the insertion mechanism or on some part of the surgical instrument manipulator assembly as the surgical instrument manipulator assembly was manually moved to unfold the drape sleeve, risked ripping the sleeve, and risked touching a non-sterile object with a sterile portion of the drape. Also, this took more time than tapping the surgical instrument manipulator assembly, and waiting for it to automatically drift in the desired direction without use of the clutch button, and without any folding and unfolding of the drape sleeve.

Figure 3B:
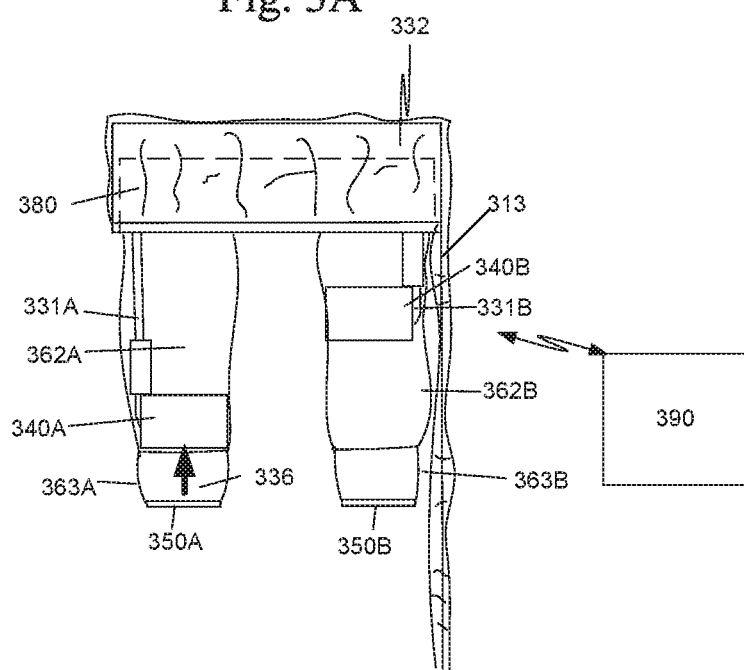

In FIGS. 3A and 3B, tapping on surgical instrument manipulator assembly 340A resulted in controller 390 automatically moving only that assembly in the direction of the tap. In another aspect, when one of the plurality of surgical instrument manipulator assemblies 340 is tapped, controller 390 moves each of plurality of surgical instrument manipulator assemblies 340 so that plurality of surgical instrument manipulator assemblies 340 move distally as a group. Alternatively, in another aspect, the graphic user interface used to initiate draping could include one or more user inputs to allow the user to group the plurality of surgical instrument manipulator assemblies into sets, where the surgical instrument manipulator assemblies in a set move distally together in response to the user tapping on any one of the surgical instrument manipulator assemblies in the set.

In the example of FIGS. 3A and 3B, it was assumed that the links in the entry guide manipulator were already draped. In the example of FIGS. 4B to 4G, the automatic motion is extended to include links of an entry guide manipulator 430 of a patient side support system 410. Patient side support system 410 is the same in each of FIGS. 4B to 4G. These drawings illustrate a time sequence of motion of links of patient side support system 410 to facilitate automatic draping of entry guide manipulator 430.

FIG. 4A is a schematic illustration of a sterile surgical drape assembly 460 that is used to drape patient side support system 410. A first sterile drape portion 461 is connected between a proximal drape support 466 and a mid-drape support 465, which is this example is a rotatable seal. A second sterile drape portion 462 is connected between mid-drape support 465 and a distal drape support 467.

In this example, proximal drape support 466 and distal drape support 467 are shown as continuous hoops or rings that are attached to the drape portions, but this is illustrative only and is not intended to be limiting. Similarly first and second sterile drape portions 461 and 462 are illustrated as each being one piece, but this also is illustrative only and is not intended to be limiting. The shapes and configuration of sterile surgical drape assembly 460 are for ease of illustrating the inventive aspects described with respect to FIGS. 4B to 4G, the actual configuration of sterile surgical drape assembly 460 will depend on the details of the patient side support system. For example, second drape portion 462 could be a plurality of drape sleeves and distal drape support 467 could be a plurality of sterile adapters as illustrated in FIGS. 3A and 3B. See also FIG. 5 and the associated description. Also, sterile surgical drape assembly 460 could include a surgical drape installation aid similar to the one disclosed in commonly filed and commonly assigned, U.S. Provisional Patent Application No. 62/362,190, filed Jul. 14, 2016, which is incorporated herein by reference in its entirety.

Proximal drape support 466, mid-drape support 465, and distal drape support 467 may be held in close proximity to each other during shipment, either permanently (requiring manual separation during draping) or temporarily (using tear-away strips that come apart during the draping process). This allows the user to hold only one of the supports to position the entire sterile surgical drape assembly.

Patient side support system 410 is part of a surgical system that includes a surgeon's console (not shown) and a controller 490. Controller 490 is interconnected to patient side support system 410 by wired (electrical or optical) or wireless connections.

A base 401 of patient side support system 410 supports an arm assembly that includes an actively controlled setup arm assembly 420 and an actively controlled manipulator arm assembly 430. Actively controlled manipulator arm assembly 430 is referred to as entry guide manipulator 430. Herein, actively controlled means that the device is under the control of a controller.

In this example, setup assembly 420 includes a first setup link 402, a rotational setup joint 403, a second setup link 404, and a third setup link 406. A first prismatic joint (not visible) moves link 402 into and out of base 401, i.e., moves link 402 in first and second directions, to adjust the vertical height of setup links 404 and 406 and thereby adjust the vertical height of entry guide manipulator 430. Rotational setup joint 403 allows positioning of coupled setup links 404 and 406. A second prismatic joint (not visible) moves setup link 406 into and out of setup link 404, i.e., moves setup link in third and fourth directions, to adjust the horizontal position of entry guide manipulator 430.

The structure of entry guide manipulator 430 is similar to entry guide manipulator 130 described above. Specifically, except as described more completely below, the configuration and operation of links 413, 415, 417, 419, joints 414, 416, 418, platform 432, the entry guide manipulator assembly, the insertion mechanisms, and plurality of surgical instrument manipulator assemblies 440 of patient side support system 410 are the same as the configuration and operation of links 113, 115, 117, 119, joints 114, 116, 118, platform 132, entry guide manipulator assembly 133, insertion mechanisms 135, and plurality of instrument manipulator assemblies 140 of patient side support system 110. Thus, the description of the configuration and operation of links 113, 115, 117, 119, joints 114, 116, 118, platform 132, entry guide manipulator assembly 133, insertion mechanisms 135, and plurality of instrument manipulator assemblies 140 of patient side support system 110 is not repeated here for the configuration and operation of links 413, 415, 417, 419, platform 432, the entry guide manipulator assembly, the insertion mechanisms, and plurality of surgical instrument manipulator assemblies 440 of patient side support system 410.

Arrows 491 define the directions used to explain the draping of patient side support system 410. Controller 490 is connected to each of the actively controlled joints in patient side support system 410, to motors that control the operation of the insertion assemblies, and to plurality of surgical instrument manipulator assemblies 440.

Herein, a single controller is referenced and described. Although described as a single controller, e.g., controllers 390, 490, and 690, it is to be appreciated that this controller may be implemented in practice by any combination of hardware, software that is executed on a processor, and firmware. Also, its functions, as described herein, may be performed by one unit or divided up among different components, each of which may be implemented in turn by any combination of hardware, software that is executed on a processor, and firmware. When divided up among different components, the components may be centralized in one location or distributed across the computer-assisted teleoperated surgical system for distributed processing purposes. A processor should be understood to include at least a logic unit and a memory associated with the logic unit. Thus, in various embodiments, a controller system (e.g. controller 390, 490, 690) includes programmed instructions (e.g., a non-transitory machine-readable medium storing the instructions) to implement some or all of the methods described in accordance with aspects disclosed herein, including instructions related to draping. Any of a wide variety of centralized or distributed data processing architectures may be employed. Similarly, the programmed instructions may be implemented as a number of separate programs or subroutines, or they may be integrated into a number of other aspects of the teleoperational systems described herein. In some embodiments, the controller system supports wireless communication protocols such as Bluetooth, Infrared Data Association (IrDA) protocol, Home Radio Frequency (HomeRF) protocol, IEEE 802.11 protocol, Digital Enhanced Cordless Telecommunications (DECT) protocol, and Wireless Telemetry protocol.

Typically, platform 432 is approximately parallel to the floor of the room in which patient side support system 410 is located and fourth link 419 is vertical. Thus, to initiate draping, link 419 is rotated counter-clockwise until a lengthwise axis of link 419 is near horizontal and platform 432 is vertical as illustrated in FIG. 4B. Here, the absolute directions are not critical and relative directions are used to denote a change in orientation and the direction of that change for example.

Mid-drape support 465 of sterile surgical drape assembly 460 is mounted on an end of platform 432 that is opposite to link 419. Alternatively, mid-drape support 465 could be mounted around platform 432. User 499 positions herself/himself a predetermined distance 495 from base 401 of patient side support system 410. Predetermined distance 495 is selected so that as user 499 holds proximal drape support 466, links 419, 417, 415, and 413 can be moved into sterile surgical drape assembly 460. Links 415 and 417 are moved so that with user 499 at predetermined distance 495, user 499 can grasp proximal drape support 466 as illustrated in FIG. 4B.

With patient side support system 410 in the configuration shown in FIG. 4B, controller 490 senses that sterile surgical drape assembly 460 is mounted on platform 432. If user 499, for example, taps on one of the links of entry guide manipulator 430 for a time sufficient to introduce a position tracking disturbance for one or more of the links, controller 490 initiates an automatic entry guide manipulator drape sequence.

Initially, in the automatic entry guide manipulator drape sequence, the goal is to drape platform 432 and link 419. To do this, entry guide manipulator 430 is lowered and platform 432 is moved to the left and rotated.

Controller 490 commands the first prismatic joint to move link 402 in the distal direction, as represented by arrow 441 (FIG. 4C), commands links 415, and 417 to be moved in the first direction, downward in FIG. 4C, and commands link 419 to be rotated further counter-clockwise. Specifically, the acute angle bounded by links 415 and 417 is increased and link 419 is rotated. The increase in the angle between links 415 and 417, i.e., the downward motion of links 415 and 417, moves platform 432 to the left relative to user 499. Thus, as platform 432 is rotated by rotation of link 419, as indicated by arrow 442, and moved to the left by the downward movement of links 415 and 417, user 499 positions proximal drape support 466 so that the motion of link 419 results in link 419 and platform 432 being draped by first portion 461 of sterile surgical drape assembly 460, as illustrated in FIG. 4C, while user 499 remains standing stationary at the predetermined position at predetermined distance 495 from base 401.

The motions of entry guide manipulator 430 in this stage of the draping process are limited so that no part of sterile surgical drape assembly 460 contacts the floor. If there is a problem with sterile surgical drape assembly 460 potentially contacting the floor, the downward motion of link 402 is adjusted to eliminate the problem in this stage of draping and then link 402 is moved further down at the end of the stage illustrated in FIG. 4D to make it easier to reach the proximal end of link 413 to complete the draping of the links of entry guide manipulator 430 in the stage illustrated in FIG. 4E.

Figure 4D:
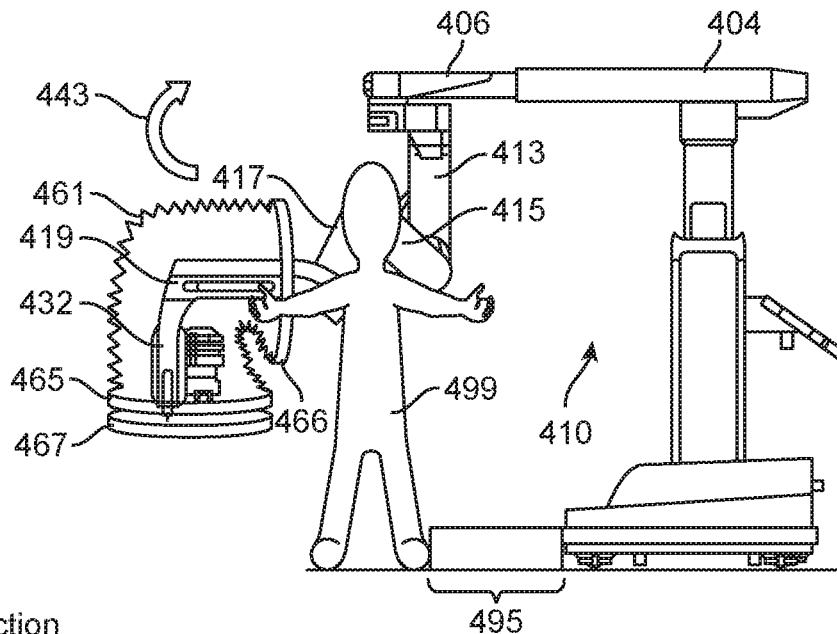
Figure 5:
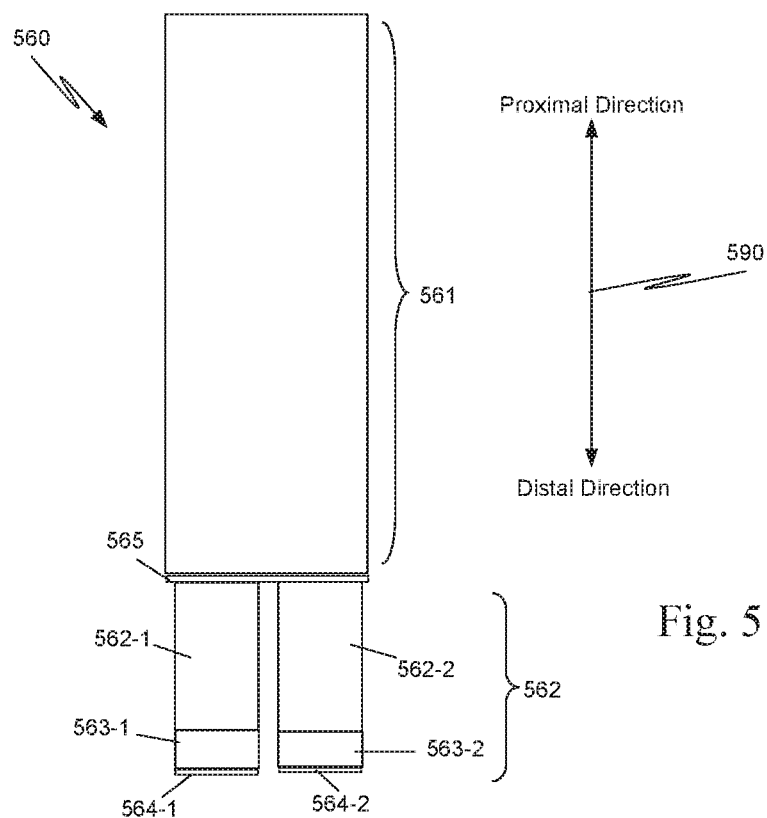
FIG. 5 illustrates another aspect of a sterile surgical drape assembly.

After platform 432 and link 419 are draped in the automatic entry guide manipulator drape sequence, the goal is to reposition links 419, 417, and 415 to facilitate the draping of links 417, 415, and 413. Thus, controller 490 commands links 415, and 417 to be moved in the second direction, upward in FIG. 4C, and commands link 419 to be rotated clockwise as indicated by arrow 443 (FIG. 4D). Specifically, the angle bounded by links 415 and 417 is decreased to an acute angle as link 419 is rotated clockwise so that link 419 is approximately parallel to the floor. The decrease in the angle between links 415 and 417, i.e., the upward motion of links 415 and 417, moves platform 432 to the right relative to user 499, as illustrated in FIG. 4D.

Figure 4E:
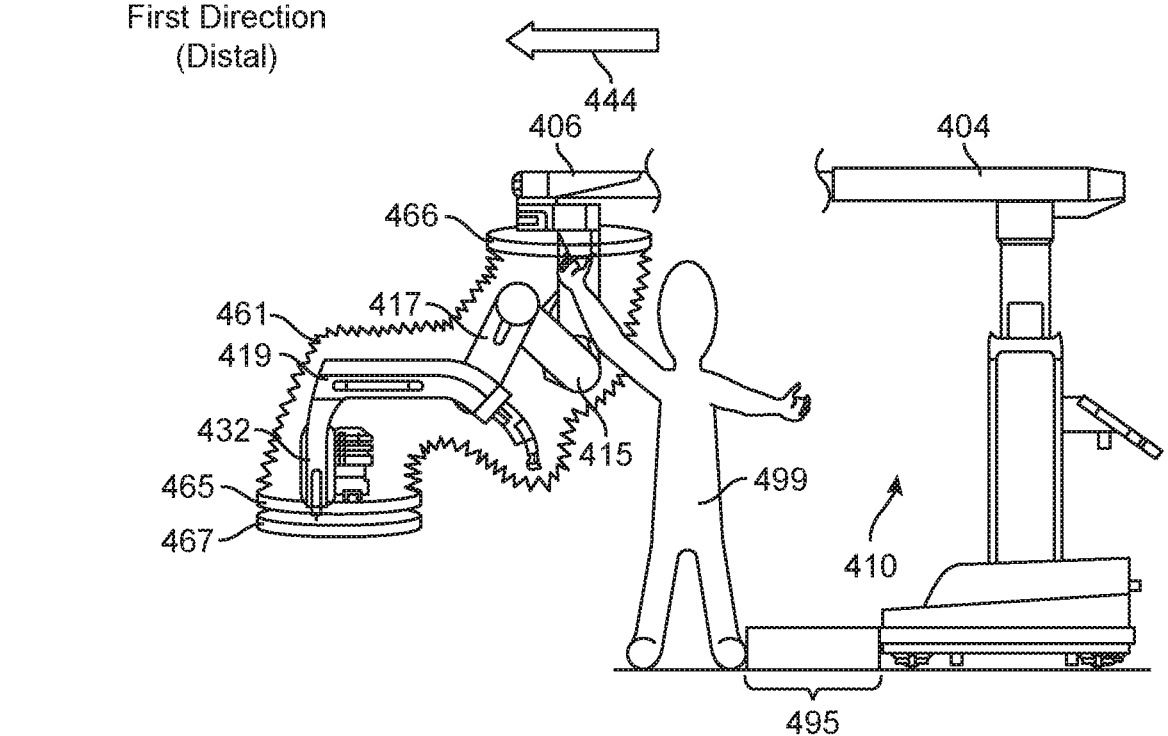

As user 499 holds proximal drape support 466 stationary and stays at predetermined distance 495 from base 401, controller 490 moves set-up link 406 to the left, e.g., controller 490 commands the second prismatic joint to move set-up link 406 in the fourth direction, as indicated by arrow 444 (FIG. 4E). As the motion of link 406 moves entry guide manipulator 430 in the fourth direction, link 419, 417, and 415 move through the open proximal end of first portion of sterile surgical drape assembly 460, and then user 499 guides the open proximal end of sterile surgical drape assembly 460 around link 413 without moving from the predetermined position at predetermined distance 495 from base 401. The user secures the open proximal end of first drape portion 461 to the proximal end of link 413.

Attaching the open proximal end of first drape portion 461 to the proximal end of link 413 send a signal to controller 490 indicating the draping of the links of entry guide manipulator 430 is complete. Thus, as illustrated in FIGS. 4B to 4E, in response to a mounting of sterile surgical drape assembly 460 on platform 432 and a subsequent position tracking disturbance of entry guide manipulator 430, controller 490 moves entry guide manipulator 430 so that each of the links of entry guide manipulator 430 passes through an open end of sterile surgical drape as the open end is held by a user standing in a stationary position. The number of links and joints in the entry guide manipulator as well as the user standing stationary are optional. The acts of automatically moving links of a manipulator by a controller through an open end of a sterile surgical drape can be adjusted to conform to the configuration of the manipulator in view of this disclosure.

In this example, after securing the open proximal end of first drape portion 461 to the proximal end of link 413, user 499 mounts mid-drape support 465 of sterile surgical drape assembly 460 around platform 432. This sends a signal to controller 490 that sterile surgical drape assembly 460 is mounted around platform 432. User 499 also removes any structures or material holding mid-drape support 465 and distal drape support 467 together.

Figure 4F:
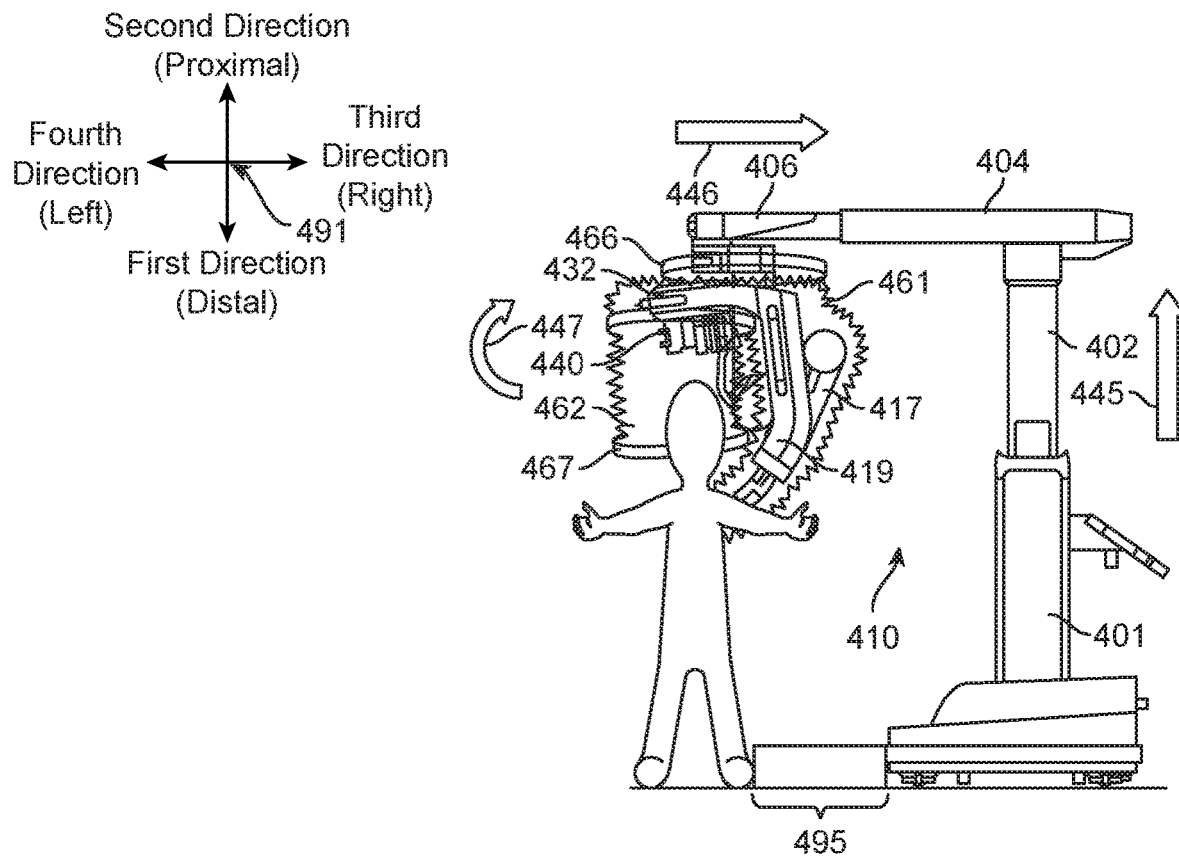

When controller 490 has received the signal indicating the draping of the links of entry guide manipulator 430 is complete and the signal indicating mid-drape support 465 of sterile surgical drape assembly 460 is mounted around platform 432, controller 490 commands the first prismatic joint to move set up link 402 in the second direction as indicated by arrow 445, commands the second prismatic joint to move setup link 406 in the third direction as indicated by arrow 446, and commands the joint controlling link 419 to rotate, as indicated by arrow 447, so that platform 432 is approximately parallel to the floor. Thus, controller 490 moves entry guide manipulator 430 to the right and up and rotates link 419 to a vertical orientation as illustrated in FIG. 4F. This causes second portion 462 of sterile surgical drape assembly 460 to extend in the distal direction, the first direction.

Figure 4G:
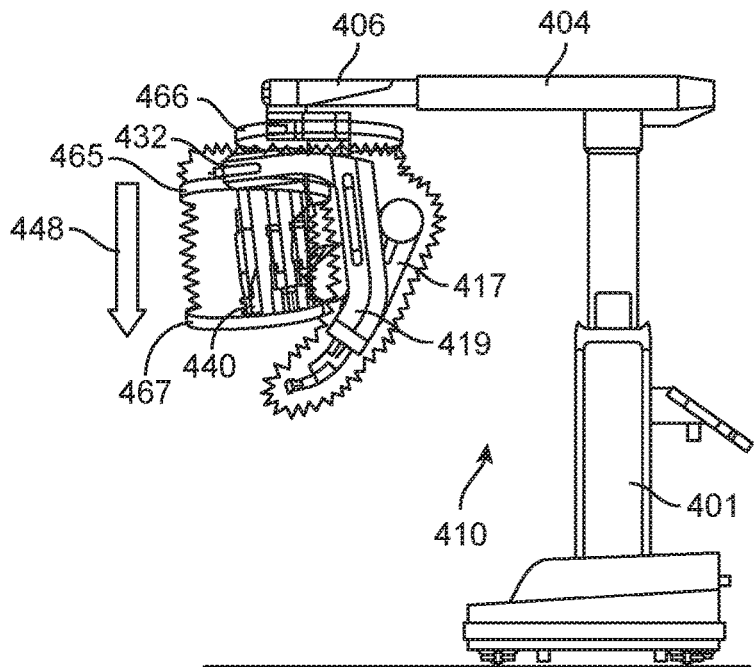

The configuration of plurality of surgical instrument manipulator assemblies 440 and second portion 462 of the sterile surgical drape are equivalent to those illustrated in FIG. 3A. Thus, controller 490 moves plurality of surgical instrument manipulator assemblies 440 in the distal direction, as indicated by arrow 448, so the distal face of each of plurality of surgical instrument manipulator assemblies 440 is adjacent distal drape support 467. Specifically, controller 490 commands each insertion assembly to move the surgical instrument manipulator assembly connected to that insertion assembly in the distal direction (FIG. 4G).

As illustrated in FIGS. 4B to 4G, user 499 stands in one place and controller 490 maneuvers manipulator components of patient side support system 410 around user 499 and into the sterile surgical drape. As controller 490 maneuvers these components, a distal portion of the sterile surgical drape stays attached to patient side support system 410 and elements of patient side support system 410 move relative to the proximal portion of the sterile surgical drape. All of these motions can be done serially or in a coordinated way.

Sterile surgical drape assembly 460 may or may not contain features that can be sensed by controller 490. There are a number of ways to accomplish this: RFID tags, metal pieces or magnets, infrared beacons, etc. Technology capable of non-contact position detection could also be used. Contact methods are also possible; e.g., the act of connecting a piece of the sterile surgical drape assembly to a component of patient side support system 410 throws a switch. When controller 490 senses the location of these features of the sterile surgical drape relative to a component of patient side support system 410, controller 490 uses that information to coordinate the motion of the components of patient side support system 410 so that the components enter the sterile surgical drape. If no sensing is available (i.e., no feedback), the draping process could be open-loop, with controller 490 maneuvering the components of patient side support system 410 through a timed sequence.

As described above, prior to use, at least a portion of a patient side support system is automatically draped with a sterile surgical drape prior to using the patient side support system in a surgical procedure. Prior to considering in further detail examples of the process flow and control systems used by a controller in automatically draping manipulator components of a patient side support system, it is helpful to consider examples of aspects of a patient side support system and a sterile surgical drape, because some of the control states are dependent upon signals provided during the draping process, as just discussed.

Figure 6A:
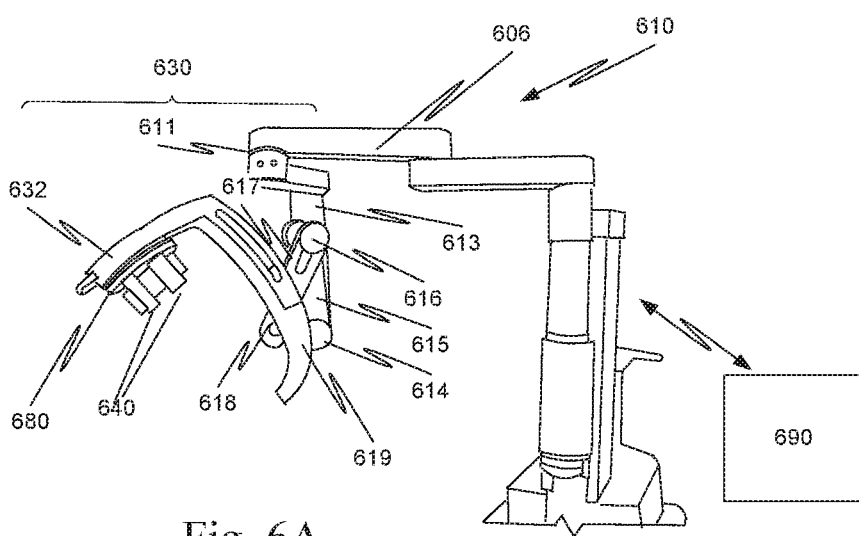
FIG. 6A is an illustration of the patient side support system in a configuration for draping.

In one aspect, a sterile surgical drape assembly 560 (FIG. 5), sometimes referred to as surgical drape assembly 560, is used to drape a portion of patient side support system 610 (FIG. 6A). In one aspect, sterile surgical drape assembly 560 includes a first portion 561 and a second portion 562.

First portion 561 of sterile surgical drape assembly 560 is connected to a stationary part of a rotatable seal 565 and second portion 562 is connected to a movable part of rotatable seal 565. In one aspect, rotatable seal 565 is labyrinth seal, where the stationary part is a roll cover portion of the labyrinth seal, and the movable part is a base comb portion of the labyrinth seal.

Second portion 562 of sterile surgical drape assembly 560, in one aspect, includes a plurality of drape sleeves 562-1, 562-2, a plurality of boots 563-1, 563-2, and a plurality of mechanical interface elements 564-1, 564-2. Typically, sterile surgical drape assembly 560 includes one drape sleeve, one boot, and one mechanical interface element for each surgical instrument manipulator assembly of plurality of surgical instrument manipulator assemblies 640.

Each of plurality of mechanical interface elements 564-1, 564-2 is coupled to a corresponding boot in plurality of boots 563-1, 563-2. Each of plurality of boots 563-1, 563-2 is coupled to a corresponding drape sleeve in plurality of drape sleeves 562-1, 562-2. An opening of each drape sleeve in plurality of drape sleeves 562-1, 562-2 is connected to the movable portion of rotatable seal 565, which, in one aspect, is a disc with ribs that form a plurality of wedge-shaped "frames" with apertures, each of the frames is sized to circumscribe a surgical instrument manipulator assembly. The open end of each of plurality of drape sleeves 562-1, 562-2 is coupled to a different one of the plurality of wedge-shaped frames. Each of plurality of boots 563-1, 563-2 fits around a surgical instrument manipulator assembly that is coupled by an insertion assembly to an entry guide manipulator assembly 680.

FIG. 6A is an illustration of a patient side support system 610 in a configuration to initiate draping in one aspect. Entry guide manipulator assembly 630, sometimes referred to as entry guide manipulator 630, includes four links 613, 615, 617, and 619 coupled by joints. As shown in FIG. 6A, a manipulator assembly yaw joint 611 is coupled between an end of setup link 606 and a second end, e.g., a proximal end, of a first manipulator link 613, sometimes referred to as link 613. Yaw joint 611 allows first manipulator link 613 to move with reference to setup link 606 in a motion that may be arbitrarily defined as "yaw" around a manipulator assembly yaw axis.

In one embodiment, setup link 606 is rotatable in a horizontal or x, y plane and yaw joint 611 is configured to allow first manipulator link 613 in entry guide manipulator 630 to rotate about a yaw axis. Setup link 606, yaw joint 611, and first manipulator link 613 provide a constantly vertical yaw axis for entry guide manipulator 630.

A first end of first manipulator link 613 is coupled to a second end of a second manipulator link 615, sometimes referred to as link 615, by a first actively controlled rotational joint 614. A first end of second manipulator link 615 is coupled to a second end of a third manipulator link 617 by a second actively controlled rotational joint 616. A first end of third manipulator link 617, sometimes referred to as link 617 is coupled to a distal portion of a fourth manipulator link 619, sometimes referred to as link 619, by a third actively controlled rotational joint 618.

In one embodiment, links 615, 617, and 619 are coupled together to act as a coupled motion mechanism. Coupled motion mechanisms are well known (e.g., such mechanisms are known as parallel motion linkages when input and output link motions are kept parallel to each other). For example, if rotational joint 614 is actively rotated, joints 616 and 618 are also actively rotated so that link 619 moves with a constant relationship to link 615. Therefore, it can be seen that the rotational axes of joints 614, 616, and 618 are parallel. When these axes are perpendicular to the rotational axis of yaw joint 611, links 615, 617, and 619 move with reference to first manipulator link 613 in a motion that may be arbitrarily defined as "pitch" around a manipulator assembly pitch axis. Since links 615, 617, and 619 move as a single assembly, first manipulator link 613 may be considered an active proximal manipulator link, and second through fourth manipulator links 615, 617, and 619 may be considered collectively an active distal manipulator link.

Figure 6B:
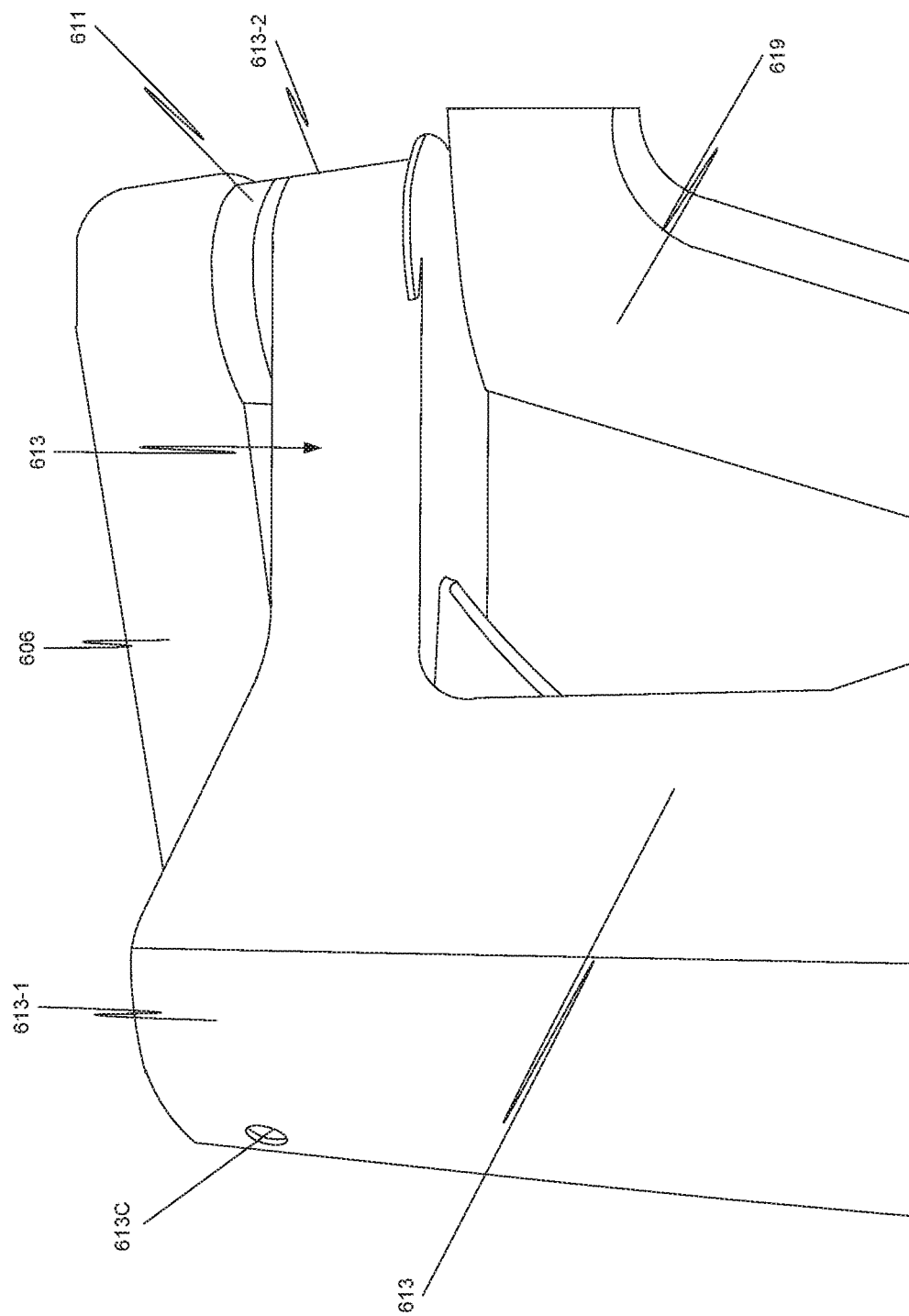
FIGS. 6B and 6C illustrate drape alignment and mounting receptacles on a link of the patient side support system of FIG. 6A.
Figure 6C:
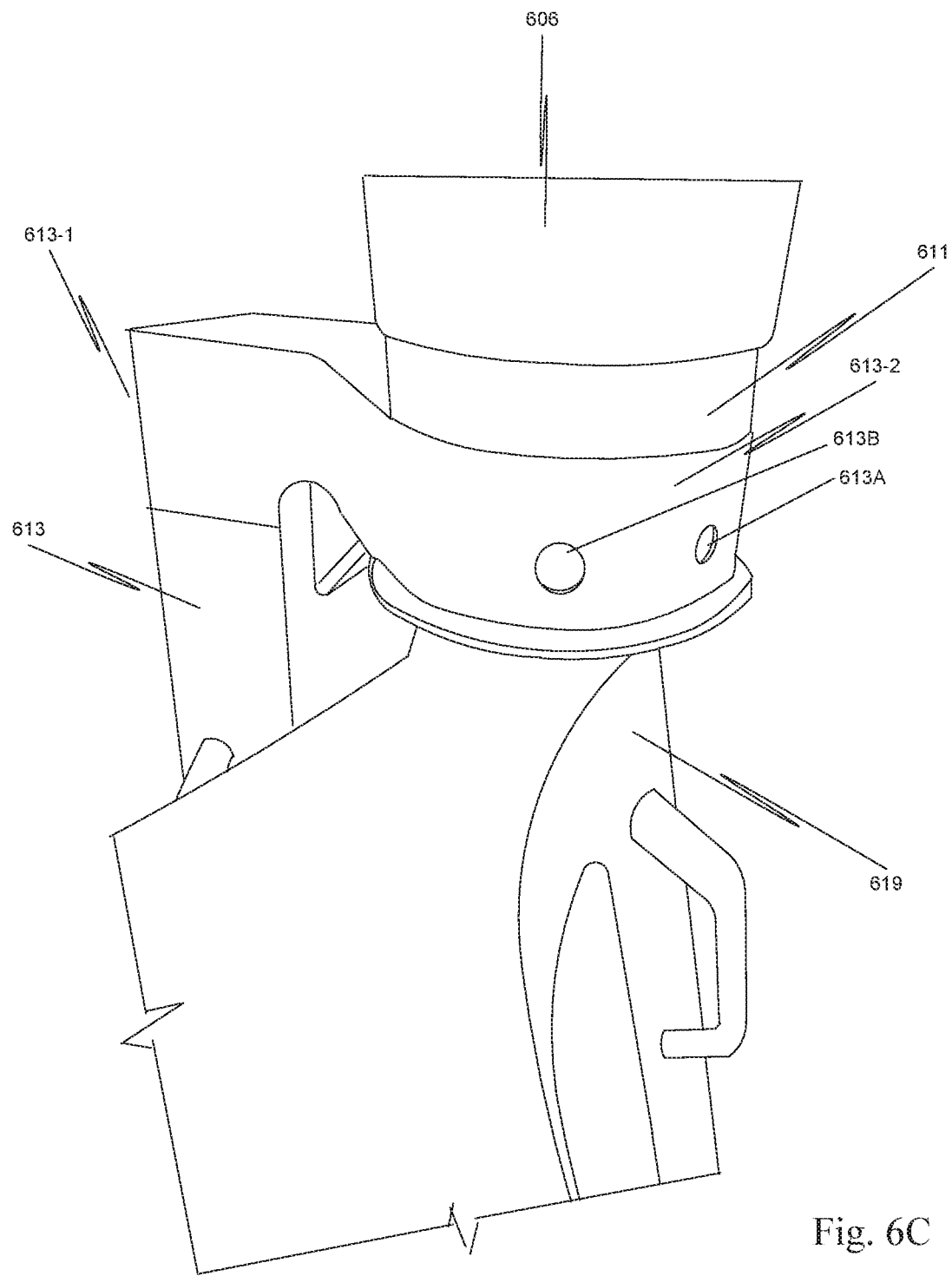

In one aspect, a first active manipulator link 613 includes a first end 613-1 (FIG. 6B) that includes an alignment receptacle 613C and a second end 613-2 (FIG. 6C) that includes two alignment receptacles 613A, 613B. Attachment devices—one for each of the alignment receptacles—are affixed to sterile surgical drape assembly 560. In one aspect, each of alignment receptacles 613A, 613B, 613C includes a magnet and the attachment devices affixed to sterile surgical drape assembly 560 are shaped to fit in alignment receptacles 613A, 613B, 613C, and are made of a metal that is attracted to and couples with the magnet.

In one aspect, each of alignment receptacles 613A, 613B, 613C includes an attachment sensor or has an attachment sensor associated with the alignment receptacle. The attachment sensor detects that sterile surgical drape assembly 560 has been attached to patient side support system 610 and when all the attachment devices are sensed, a drape attached signal is sent to controller 690 indicating the attachment of sterile surgical drape assembly 560 to the links of the entry guide manipulator is complete. Specifically, when an attachment device attached to sterile surgical drape assembly 560 is engaged with the corresponding alignment receptacle to attach sterile surgical drape assembly 560 to a portion of patient side support system 610, the attachment sensor detects the presence of the attachment device, and when all the attachment devices have been detected, a drape attached signal is transmitted.

A sensor configured to detect the presence of a drape attachment device may be, for example, an inductive sensor. An inductive sensor emits a magnetic field that is sensed by the sensor, such as via an induction loop. When a metallic member, i.e., the attachment device, is proximate the sensor, the metallic member changes the inductance, which is detected by the sensor to indicate the presence of the attachment device. The use of an inductive sensor is illustrative only and is not intended to be limiting.

A sensor to detect the attachment of sterile surgical drape assembly 560 may be, for example, an optical sensor. An optical sensor may use, for example, light reflected off the drape attachment device or light reflected off sterile surgical drape assembly 560 itself to detect when sterile surgical drape assembly 560 has been attached. In another example, an optical sensor may be a sensor that emits a light beam and receives the light beam, but senses the presence of sterile surgical drape assembly 560 when sterile surgical drape assembly 560 or the attachment device breaks the beam. A sensor may also be a capacitive sensor that senses a change in capacitance that occurs when surgical drape assembly 560 has been attached. In another example, a sensor may be a switch that is mechanically depressed or otherwise switched by the drape attachment device or sterile surgical drape assembly 560 when sterile surgical drape assembly 560 is attached to first manipulator link 613 of patient side support system 610.

Figure 7A:
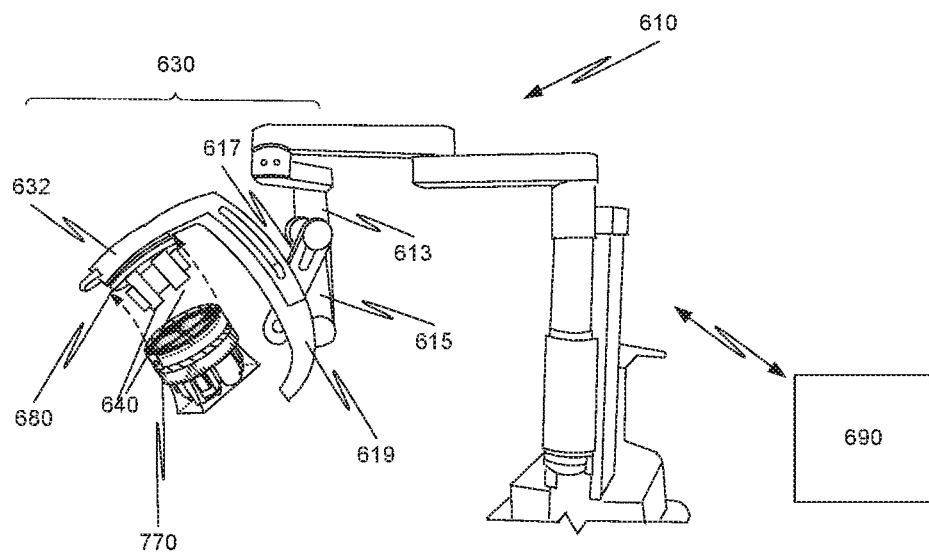
FIG. 7A illustrates a surgical drape installation package being moved into position for mounting on a platform on one end of a link the patient side support system of FIG. 6A.

FIG. 7A illustrates a surgical drape installation package 770 being moved into position for mounting on platform 632 on one end of link 619. Surgical drape installation package 770 includes a surgical drape installation aid on which sterile surgical drape assembly 560 is mounted.

Figure 7B:
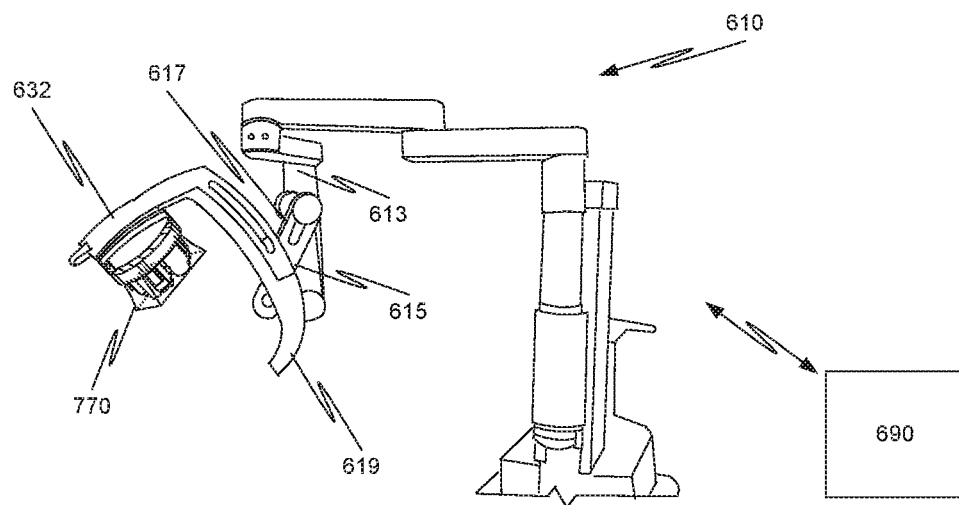
FIG. 7B shows the surgical drape installation package mounted on the platform of FIG. 7A.

FIG. 7B shows surgical drape installation package 770 mounted on platform 632. In particular, each of a plurality of latches of rotatable seal 565 has been engaged in a corresponding latch receptacle in platform 632. An example of a surgical drape installation package is presented in commonly assigned and commonly filed U.S. Provisional Patent Application No. 62/362,190, filed Jul. 14, 2016, which is incorporated herein by reference in its entirety.

When surgical drape installation package 770 is mounted on platform 632, a drape mount sensor sends a drape mounted signal to controller 690 indicating the mounting of surgical drape installation package 770. In one aspect, the drape mount sensor includes a mechanical switch, e.g., a plunger, which is activated by mounting of the stationary part of a rotatable seal 565. Alternatively, instead of a mechanical sensor, the drape mount sensor could be an inductive sensor, a capacitive sensor, or an optical sensor similar to those described above.

In the example of FIGS. 7A and 7B, controller 690, in response to a user input to initiate draping, moves link 619 so that a roll axis of plurality of surgical instrument manipulator assemblies 640 is at about a 45 degree angle with respect to the floor and moves each of plurality of surgical instrument manipulator assemblies 640 as far apart as possible. However, in another aspect, controller 690, in response to a user input to initiate draping, moves link 619 so that the roll axis of plurality of surgical instrument manipulator assemblies 640 is approximately perpendicular to the floor and moves each of plurality of surgical instrument manipulator assemblies 640 as far apart as possible. For some users, it is easier to mount surgical drape installation package 770 on platform 632 with platform 632 approximately parallel to the floor rather than at the angle shown in FIG. 7A. Here, approximately perpendicular and approximately parallel, means perpendicular and parallel as viewed by a user of patient side support system 610, which may not be precisely perpendicular and/or precisely parallel.

After the user mounts surgical drape installation package 770 on platform 632, the user taps, pushes, on link 619. Controller 690 senses a position tracking disturbance created by the tap, and in response moves platform into the appropriate position to initiate draping, e.g., the position illustrated in FIG. 7B.

Thus, in this aspect, controller 690 moves a component or components, sometimes referred to as a part or parts, of a patient side support system to a configuration that facilitates draping the component or components by the user. Controller 690 moves (drifts) the component or components of a patient side support system through a sequence of configurations to facilitate installation and mating of different drape assemblies, with the benefit of a streamlined and more robust workflow, in response to a user momentarily applying a force on, e.g. tapping, the component or components. As just described, the movement may not result in the component or components being moved into or within the sterile surgical drape assembly. Controller 690 is configured to automatically move a component or components of patient side support system 610 into a position to facilitate draping in response to each time a user causes a position tracking disturbance by momentarily applying a force on that component or components. Various methods to implement the drifting of the user tapped component are described more completely below.

Figure 8:
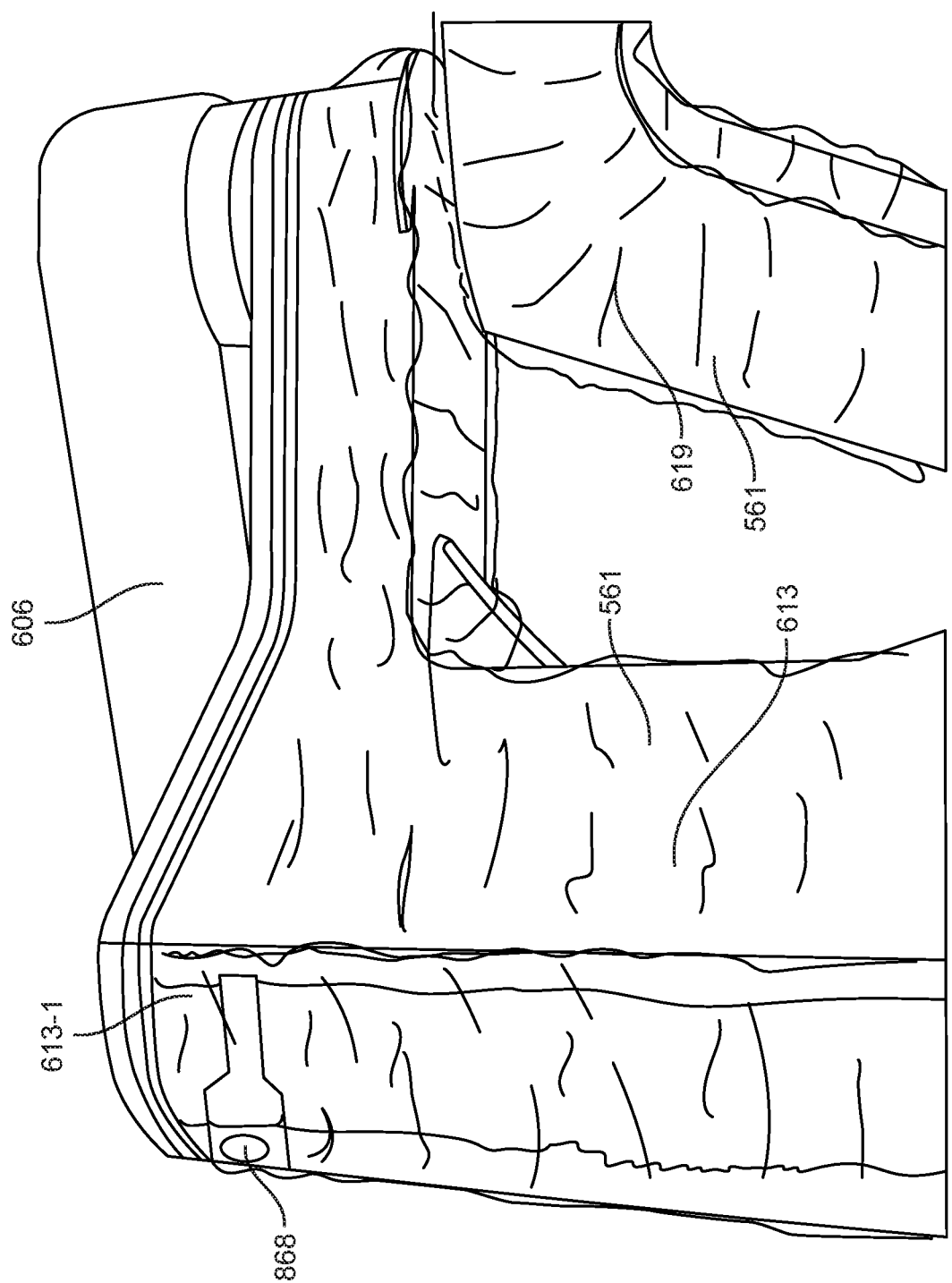
FIG. 8 is an illustration showing the draped links of the entry guide manipulator of FIGS. 6A and 7A.

FIG. 8 is an illustration showing that links 619, 617, 615, and 613 of entry guide manipulator 630 have been draped. An drape attachment device 868 is mounted in alignment receptacle 613C, and so controller 690 has received a signal indicating the draping of the links of entry guide manipulator 630 is complete and a signal indicating rotatable seal 565 of sterile surgical drape assembly 560 is mounted around platform 632

Figure 9A:
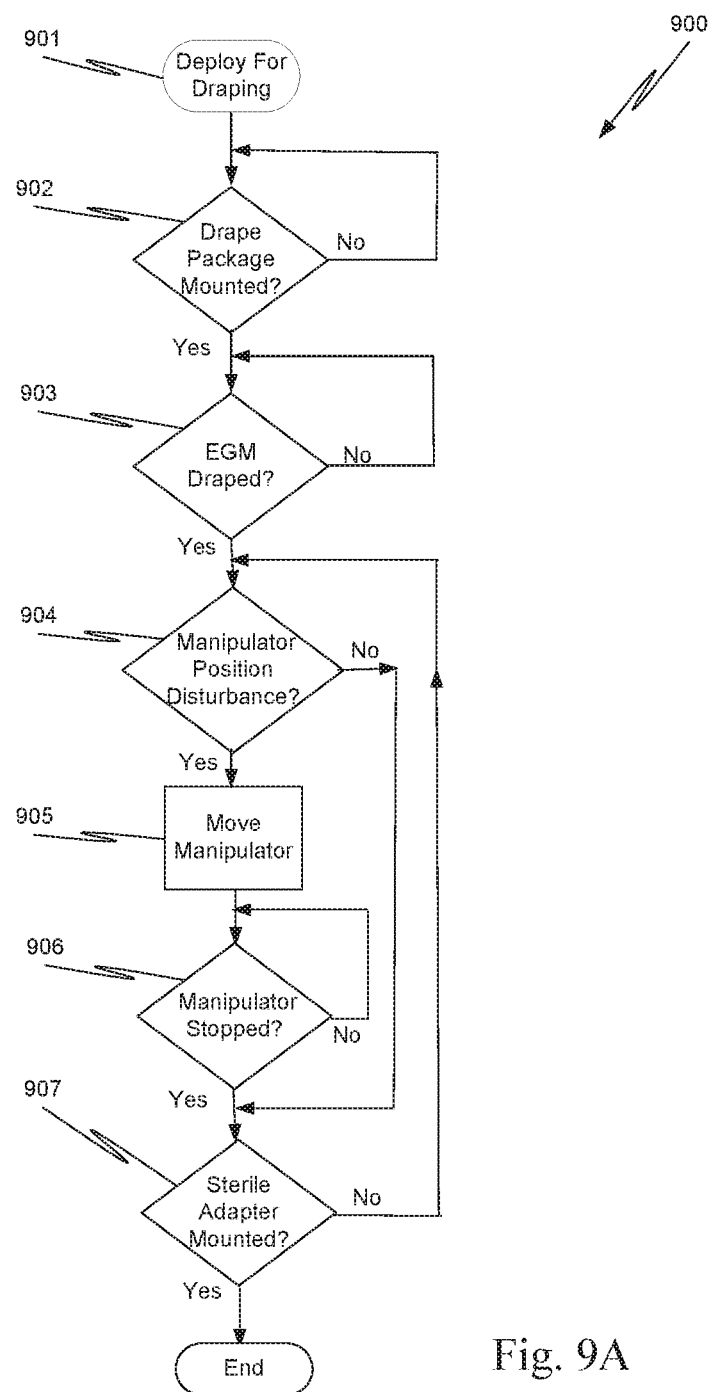
FIG. 9A is a process flow diagram of a method used by a controller to implement the acts described with respect to FIGS. 3A and 3B.

FIG. 9 is a process flow diagram of a method 900 used by controller 690 to implement the acts described above with respect to FIGS. 3A and 3B. Method 900 is entered when a user selects a DEPLOY FOR DRAPING option 901 in a graphic user interface for patient side support system 610. In response to the selection of DEPLOY FOR DRAPING option 901, controller 690 configures patient side support system 610 by rotating link 619 and commanding entry guide manipulator assembly 680 to move each of plurality of surgical instrument manipulator assemblies 640 as far apart as possible. Controller 690 transitions to DRAPE PACKAGE MOUNTED check process 902.

Controller 690 waits in DRAPE PACKAGE MOUNTED check process 902 until a signal is received from patient side support system 610 indicating that surgical drape installation package 770 has been mounted on platform 632. When this signal is received, it means that the draping process can begin. When the signal is received from patient side support system 610 indicating that surgical drape installation package 770 has been mounted on platform 632, controller 690 transitions from DRAPE PACKAGE MOUNTED check process 902 to ENTRY GUIDE MANIPULATOR (EGM) DRAPED check process 903.

DRAPE PACKAGE MOUNTED check process 902 should not be interpreted as requiring polling to determine whether surgical drape installation package 770 has been mounted on platform 632. In one aspect, an event handler is used to detect an event that is fired when the signal from patient side support system 610 indicates surgical drape installation package 770 has been mounted on platform 632. When this event is detected controller 690 transitions from DRAPE PACKAGE MOUNTED check process 902 to ENTRY GUIDE MANIPULATOR (EGM) DRAPED check process 903.

Controller 690 waits in ENTRY GUIDE MANIPULATOR (EGM) DRAPED check process 903 until a signal is received from patient side support system 610 indicating that the proximal end of first portion 561 of sterile surgical drape assembly 560 is attached to the proximal end of link 613. When this signal is received, controller 690 transitions from ENTRY GUIDE MANIPULATOR (EGM) DRAPED check process 903 to MANIPULATOR POSITION DISTURBANCE check process 904.

ENTRY GUIDE MANIPULATOR (EGM) DRAPED check process 903 should not be interpreted as requiring polling to determine whether the proximal end of first portion 561 of sterile surgical drape assembly 560 is attached to the proximal end of link 613. In one aspect, an event handler is used to detect an event that is fired when the signal from patient side support system 610 indicates the proximal end of first portion 561 of sterile surgical drape assembly 560 is attached to the proximal end of link 613. (Arrow 590 (FIG. 5) defines the proximal and distal directions as used with respect to sterile surgical drape assembly 560.) When this event is received, controller 690 transitions from ENTRY GUIDE MANIPULATOR (EGM) DRAPED check process 903 to MANIPULATOR POSITION DISTURBANCE check process 904.

In MANIPULATOR POSITION DISTURBANCE check process 904, controller 690 determines whether the position of a surgical instrument manipulator assembly of plurality of surgical instrument manipulator assemblies 640 has changed by more than a predetermined amount from a known position of that surgical instrument manipulator assembly, e.g., if a position tracking disturbance exceeds a specified threshold. If the position has not changed, controller 690 transitions from MANIPULATOR POSITION DISTURBANCE check process 904 to STERILE ADAPTER MOUNTED check process 907. If the position of the surgical instrument manipulator assembly changes by more than a predetermined amount from the known position, controller 690 transfers from MANIPULATOR POSITION DISTURBANCE check process 904 to MOVE MANIPULATOR process 905.

In MOVE MANIPULATOR process 905, controller 690 moves the insertion assembly to which the surgical instrument manipulator assembly of plurality of surgical instrument manipulator assemblies 640 is attached in the direction indicated by the position tracking disturbance. This causes the surgical instrument manipulator assembly to move within the drape sleeve. After motion of the insertion mechanism is initiated, controller 690 transitions from MOVE MANIPULATOR process 905 to MANIPULATOR STOPPED check process 906.

In MANIPULATOR STOPPED check process 906, controller 690 determines whether the motion of the surgical instrument manipulator assembly has stopped. The motion of the surgical instrument manipulator assembly can stop for multiple reasons: the surgical instrument manipulator assembly has reached the maximum distance of travel allowed during the draping process; the user stopped the motion by grasping the surgical instrument manipulator assembly; or something inhibited the movement of the surgical instrument manipulator assembly. Controller 690 waits in MANIPULATOR STOPPED check process 906 until the movement of the surgical instrument manipulator assembly stops or decreases to less than a predetermined threshold, and then transfers to STERILE ADAPTER MOUNTED check process 907.

MANIPULATOR STOPPED check process 906 should not be interpreted as requiring polling to determine whether the motion of the surgical instrument manipulator assembly has stopped. In one aspect, an event handler is used to detect an event that is fired when the movement of the surgical instrument manipulator assembly stops or decreases to less than a predetermined threshold, and when the event is detected, controller 690 transitions from MANIPULATOR STOPPED check process 906 to STERILE ADAPTER MOUNTED check process 907.

Controller 690 determines in STERILE ADAPTER MOUNTED check process 907 whether a signal has been received from patient side support system 610 indicating that the sterile adapter assembly has been mounted on the surgical instrument manipulator assembly. If the signal is received, method 900 ends, and otherwise controller 690 transfers from STERILE ADAPTER MOUNTED check process 907 to MANIPUALTOR POSITION DISTURBANCE check process 904.

It is possible that the surgical instrument manipulator assembly was stopped in a position other than the position where it is easy to mount the sterile adapter assembly. Thus, when controller 690 transitions from STERILE ADAPTER MOUNTED check process 907 to MANIPUALTOR POSITION DISTURBANCE check process 904, MANIPUALTOR POSITION DISTURBANCE check process 904 determines whether the user has again tapped the surgical instrument manipulator assembly to move the assembly in a particular direction.

The transitions between MANIPUALTOR POSITION DISTURBANCE check process 904 and STERILE ADAPTER MOUNTED check process 907 should not be interpreted as requiring a polling loop between the two processes. As described for the other check processes, an event handler is used to detect an event and then controller 690 takes the appropriate action based on the event that was received.

Figure 9B:
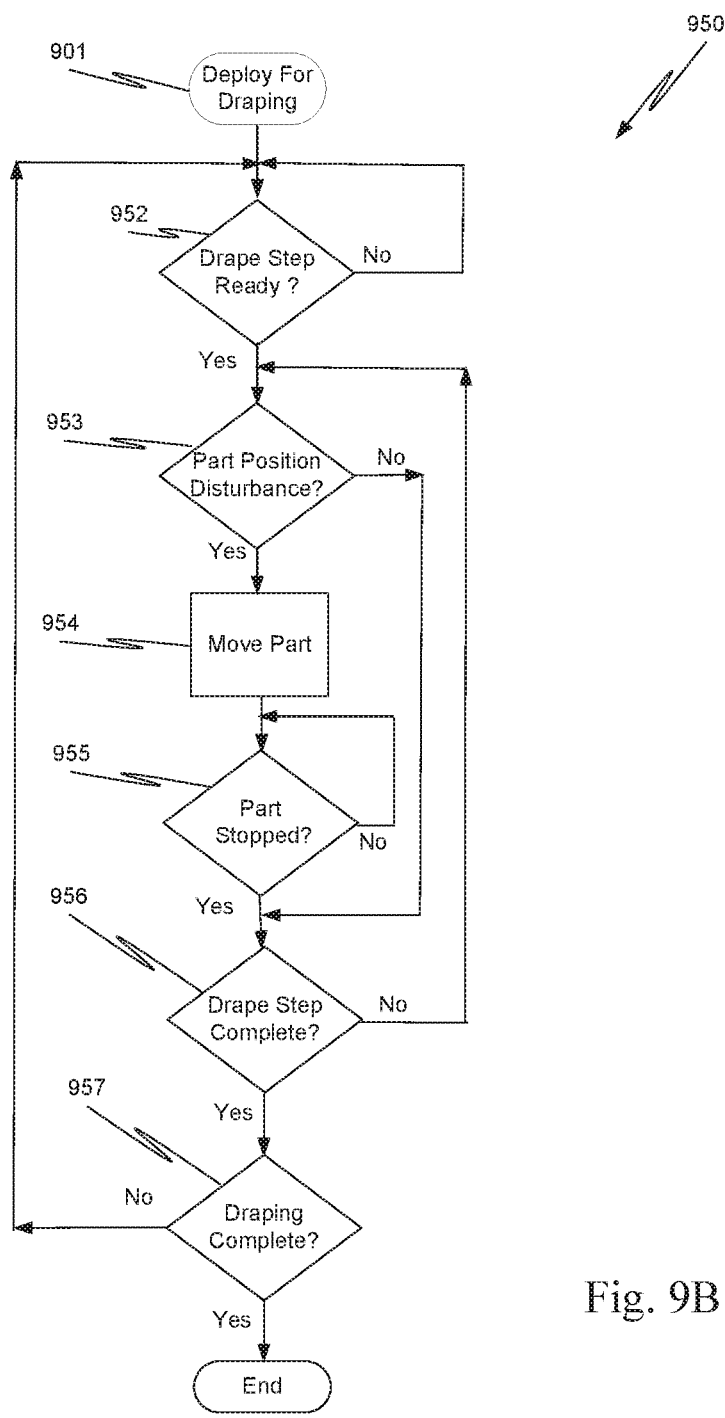
FIG. 9B is a process flow diagram of a method used by a controller, in one aspect, to facilitate steps in draping of the configurations illustrated in FIGS. 3A and 3B, FIGS. 4B to 4G, and 6A.

While method 900 has been described with respect to moving a surgical instrument manipulator assembly within a drape sleeve, acts 904 to 906 can be used with respect to movement of any component of patient side support system 610 to move that component into a position to facilitate draping. FIG. 9B is a process flow diagram of a method 950 used by controller 690, in one aspect, to facilitate steps in draping of the configurations illustrated in FIGS. 3A and 3B, FIGS. 4A to 4G, and 6A. In particular, for example, movements of a part of parts of the patient side support system being draping and illustrated in these figures can be controlled using method 950.

In the description of method 950, the draping process in divided into a sequence of steps referred to as draping steps. As used here, a step may include one or more acts. Also, a part is a component or group of components of the patient side support system that is being draped. Depending on the draping step, a part can be, for example, a surgical instrument manipulator assembly, one or more of the link of the patient side support system, the entry guide manipulator, etc. In one aspect, a part of a patient side support system that is moved in response to the user momentarily applying a force on the part in a direction of desired movement of that part is referred to as a manipulator component.

In one aspect, method 950 also is entered when a user selects a DEPLOY FOR DRAPING option 901 in a graphic user interface for patient side support system 610. In response to the selection of DEPLOY FOR DRAPING option 901, controller 690 configures patient side support system 610 by commanding entry guide manipulator assembly 680 to move each of plurality of surgical instrument manipulator assemblies 640 as far apart as possible. Controller 690 transitions to DRAPE STEP READY check process 952.

Controller 690 waits in DRAPE STEP READY check process 952 until an event is received indicating that the draping process is ready for a draping step that includes movement of a part of the patient side support system. For example, in one aspect, following completion of DEPLOY FOR DRAPING option 901, platform 632 is approximately parallel to the floor of the room in which patient side support system 610 is located and fourth link 619 is vertical, as described above. This facilitates mounting surgical drape installation package 770 on platform 632 for some users.

As explained above, when surgical drape installation package 770 is mounted on platform 632, a drape mount sensor sends a drape mounted signal to controller 690. The drape mounted signal is an event, which indicates to controller 690 that the draping process is ready for a draping step that includes movement of a part of the patient side support system, e.g., movement of link 619 to a forty-five degree position. Hence, for this example, controller 690 remains in DRAPE STEP READY check process 952 until the drape mounted signal is received, and then transitions to PART POSITION DISTURBANCE check process 953.

DRAPE STEP READY check process 952 should not be interpreted as requiring polling to determine whether patient side support system 610 is ready for the next drape step. In one aspect, an event handler is used to detect an event indicating that patient side support system 610 is ready for the next draping step. When this event is detected controller 690 transitions from DRAPE STEP READY check process 952 to PART POSITION DISTURBANCE check process 953.

In PART POSITION DISTURBANCE check process 953, controller 690 determines whether a position change indication has been detected. If controller 690 detects a position change indication, controller 690 transitions to MOVE PART process 954, and otherwise transitions to DRAPE STEP COMPLETE check process 956.

Controller 690 can detect a position change indication in several different ways. As explained above, controller 690 knows the position and velocity of the part. If the position of the part changes by more than a predetermined amount from the known position due to a user applying a momentary force on the part in a direction of desired movement of the part, e.g., tapping on the part, controller 690 detects a position change indication, e.g., a part position disturbance. In some aspects, the part may include one or more instances of some type of a motion control input device that a user can use to indicate a desired direction of movement of the part, e.g., a pressure switch, a touch pad, and when controller 690 detects a signal from such a motion control input device, controller 690 detects a position change indication. In some aspects, the motion control input device is on a portion of the part that is covered by the surgical drape during use; in some aspects, the motion control input device is on a portion of the part that is not covered by the surgical drape during use.

In MOVE PART process 954, controller 690 moves the part in the direction indicated by the position change indication. This causes the part to move in the user specified direction. After motion of the part is initiated, controller 690 transitions from MOVE PART process 954 to PART STOPPED check process 955.

In PART STOPPED check process 955, controller 690 determines whether the motion of the part has stopped. The motion of the part can stop for multiple reasons: the part has reached the maximum distance of travel allowed during this draping step; the user stopped the motion by grasping the part; or something inhibited the movement of the part. Controller 690 waits in PART STOPPED check process 955 until the movement of the part stops or decreases to less than a predetermined threshold, and then transfers to DRAPE STEP COMPLETE check process 956.

PART STOPPED check process 956 should not be interpreted as requiring polling to determine whether the motion of the part has stopped. In one aspect, an event handler is used to detect an event that is fired when the movement of the part stops or decreases to less than a predetermined threshold, and when the event is detected, controller 690 transitions from PART STOPPED check process 955 to DRAPE STEP COMPLETE check process 956.

In DRAPE STEP COMPLETE check process 956, controller 690 determines whether an event has been received indicating that the drape step is complete. If the event is received, DRAPE STEP COMPLETE check process 956 transfers to DRAPING COMPLETE check process 957, and otherwise controller 690 transfers from DRAPE STEP COMPLETE check process 956 to PART POSITION DISTURBANCE check process 953.

It is possible that the part was stopped in a position other than the position needed for the drape step. Thus, when DRAPE STEP COMPLETE check process 956 transfers to PART POSITION DISTURBANCE check process 953, PART POSITION DISTURBANCE check process 953 determines whether the user has again, for example, tapped the part to indicate the direction of desired motion of the part.

The transitions between PART POSITION DISTURBANCE check process 953 and DRAPE STEP COMPLETE check process 956 should not be interpreted as requiring polling between the two processes. As described for the other check processes, an event handler is used to detect an event and then controller 690 takes the appropriate action based on the event that was received.

When DRAPE STEP COMPLETE check process 956 transfers to DRAPING COMPLETE check process 957, controller 690 determines whether a draping complete event has been detected. If the draping complete event has been detected, controller 690 ends method 950 and otherwise transfers to DRAPE STEP READY check process 952.

In the above example, controller 690 transitioned from DRAPE STEP READY check process 952 to PART POSITION DISTURBANCE check process 953, when an event was received indicating that surgical drape installation package 770 was mounted on platform 632. When a user taps on the right side of link 619 (FIG. 6A), controller 690 detects a position change indication, because the tapping causes the position of link 619 to change from a known position of link 619 for at least a predetermined time interval. (Aspects used to identify the predetermined time interval and displacement are described more completely below.) Thus, controller 690 transitions from PART POSITION DISTURBANCE check process 953 to MOVE PART process 954.

In MOVE PART process 954, controller 690 moves link 619 to the forty-five degree position illustrated in FIG. 6A. Controller 690 stops movement of link 619 when link 619 reaches the desired orientation, and controller 690 transitions from PART STOPPED check process 955 transfers to DRAPE STEP COMPLETE check process 956.

Since the positioning of link 619 completes the draping step, controller 690 transitions from DRAPE STEP COMPLETE check process 956 to DRAPING COMPLETE check process 957. Controller 690 transitions from DRAPING COMPLETE check process 957 to DRAPE STEP READY check process 952.

The next draping step that utilizes detection of a position tracking disturbance depends on how the draping steps are defined. For example, if the automated sequence of FIGS. 4B to 4F is used to drape links 613, 615, 617, and 619, controller 690 would transition from DRAPE STEP READY check process 957 to PART POSITION DISTURBANCE check process 953, and wait until a user again taps on link 619 to start the automated movement of these links into a portion of the drape. Alternatively, the draping of links 613, 615, 617, and 619 could be divided into a sequence of steps where draping of each of link or some subgroup of the links is treated as a draping step in method 950.

If the automated sequence of FIGS. 4B to 4F is not used to drape links 613, 615, 617, and 619, controller 690 would remain in DRAPE STEP READY check process 957 until an event is received indicating that links 613, 615, 617, and 619 have been draped and that the drape sleeves are deployed. Then, controller 690 would transition from DRAPE STEP READY check process 957 to PART POSITION DISTURBANCE check process 953 to determine when a user tapped on a surgical instrument manipulator assembly to move the surgical instrument manipulator assembly within the sleeve.

Figure 10:
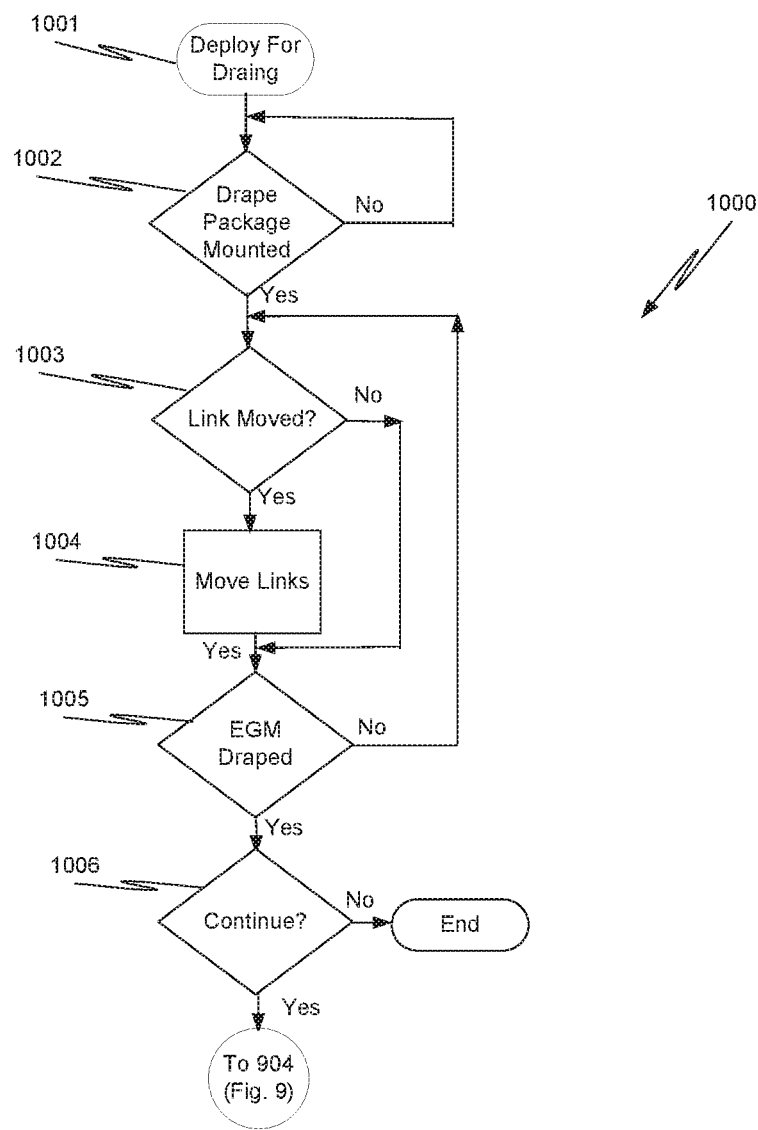
FIG. 10 is a process flow diagram of a method used by a controller to implement the acts described with respect to FIGS. 4B to 4G.

FIG. 10 is a process flow diagram of a method 1000 used by controller 690 to implement the acts described above with respect to FIGS. 4B to 4G. In FIG. 10, the various check processes should not be interpreted as requiring polling. As explained above, the check processes can be implemented using an event handler.

Method 1000 is entered with a user selects a DEPLOY FOR DRAPING option 1001 in a graphic user interface for patient side support system 610. In response to the selection of DEPLOY FOR DRAPING option 1001, controller 690 configures patient side support system 610 by rotating link 619 and commanding entry guide manipulator assembly 680 to move plurality of surgical instrument manipulator assemblies 640 as far apart as possible. Controller 690 transitions to DRAPE PACKAGE MOUNTED check process 1002.

DRAPE PACKAGE MOUNTED check process 1002 is similar to DRAPE PACKAGE MOUNTED check process 902. Controller 690 waits in DRAPE PACKAGE MOUNTED check process 1002 until a signal is received from patient side support system indicating that surgical drape installation package 770 has been mounted on platform 632. When the signal is received from patient side support system 610 indicating that surgical drape installation package 770 has been mounted, it means that patient side support system 610 is ready to start the draping of the links of entry guide manipulator 630. When the signal is received, controller 690 transitions from DRAPE PACKAGE MOUNTED check process 1002 to LINK MOVED check process 1003.

In this example, it is assumed that the automated draping of the links of entry guide manipulator 630 is initiated by the user displacing, for example, link 619 in the distal direction. If controller 690 detects a position tracking disturbance with respect to a link of entry guide manipulator 630, controller 690 transitions from LINK MOVED check process 1003 to MOVE LINKS process 1004. Alternatively, a user could activate a switch, select a command in a graphic user interface, move the proximal end of the drape so that a switch is activated, or perhaps issue an oral command to controller 690 so that controller 690 could ascertain whether to transfer from LINK MOVED check process 1003 to MOVE LINKS process 1004. If LINK MOVED check process 1003 does not receive a signal indicating to proceed with automatic draping, LINK MOVED check process 1003 transfers to ENTRY GUIDE MANIPULATOR (EGM) DRAPED check process 1005.

The implementation of MOVE LINKS process 1004 depends on the technique used to move links 619, 617, 615, and 613 to achieve the automated draping. If an open-loop sequence is used, controller 690 maneuvers links into a first portion 561 of sterile surgical drape assembly 560 through a timed sequence motion of the links of patient side support system 610. If sensing is used, controller 690 maneuvers links into first portion 561 of sterile surgical drape assembly 560 based on the sensor signals that are received by controller 690. In each instance, links 619, 617, 615, and 613 are moved into sterile surgical drape assembly 560 in a manner equivalent to that illustrated in FIGS. 4B to 4G. Controller 690 transfers from MOVE LINKS process 1004 to EGM DRAPED process 1005.

In ENTRY GUIDE MANIPULATOR (EGM) DRAPED check process 1005, if a signal is received from patient side support system 610 indicating that the proximal end of first portion 561 of sterile surgical drape assembly 560 is attached to the proximal end of link 613, ENTRY GUIDE MANIPULATOR (EGM) DRAPED check process 1005 transitions to CONTINUE check process 1006. If a signal is not received from patient side support system 610 indicating that the proximal end of first portion 561 of sterile surgical drape assembly 560 is attached to the proximal end of link 613, ENTRY GUIDE MANIPULATOR (EGM) DRAPED check process 1005 transitions to LINK MOVED check process 1003.

When processing reaches CONTINUE check process 1006, the links of entry guide manipulator 630 have been automatically draped, and first portion 561 is secured to the proximal end of link 613. At this point, the user may have indicated to stop or delay the draping process, and so method 1000 ends. Conversely, if the user did not indicate to stop, CONTINUE check process 1006 transfers to MANIPULATOR POSITION DISTURBANCE check process 904. The method continues as described with respect to FIG. 9.

Figure 11:
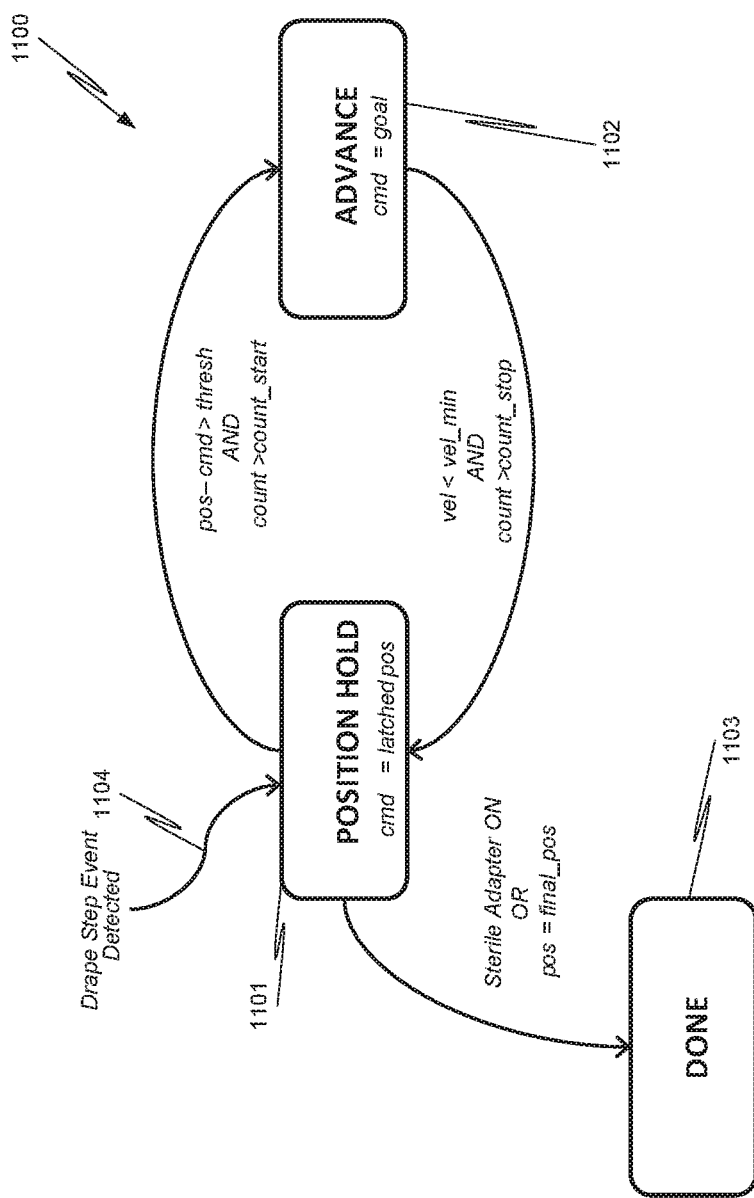
FIGS. 11 and 12 are alternative implementations of a state machine in a controller that is used to perform the methods of FIGS. 9 and 10.
Figure 12:
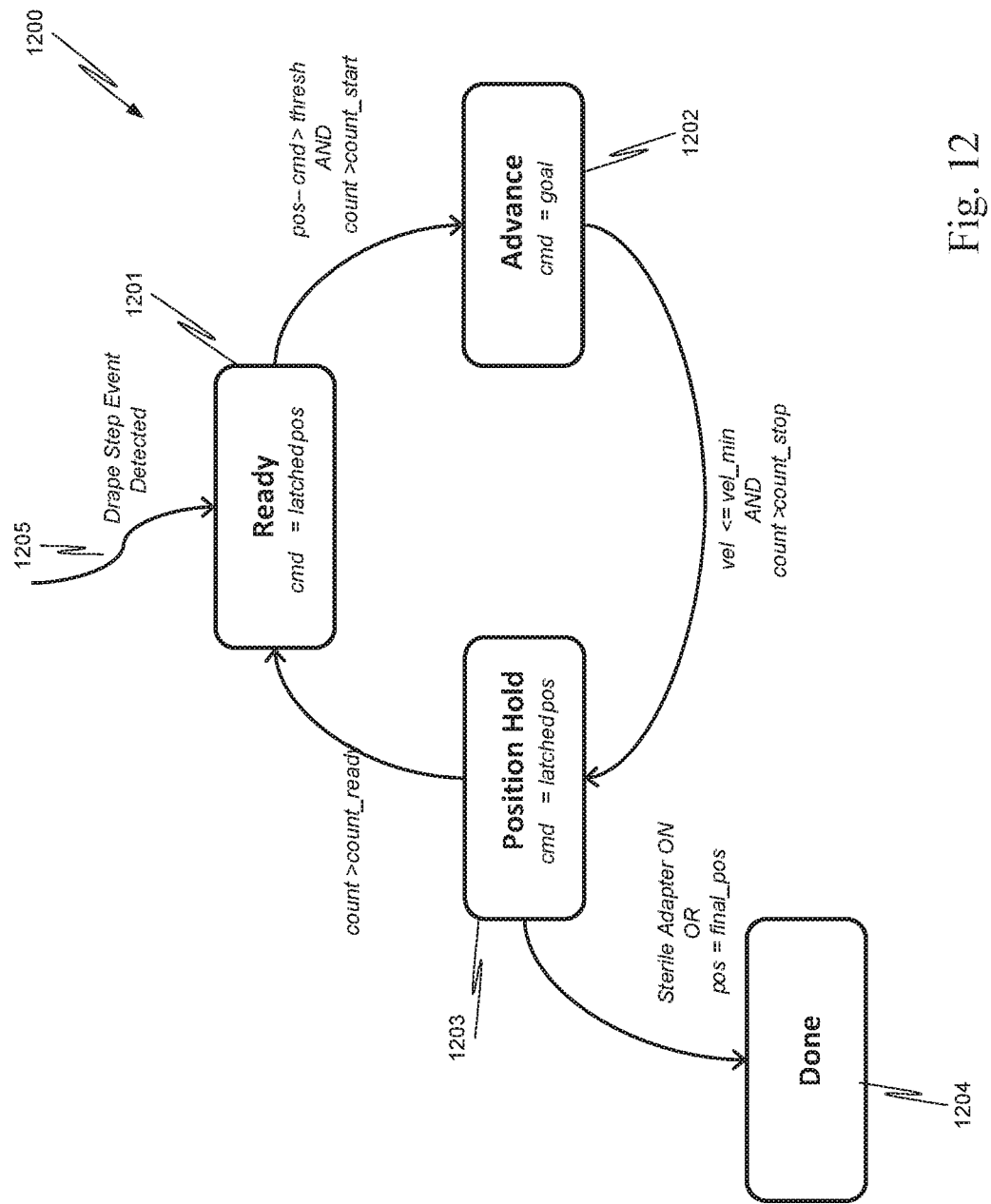
Figure 13:
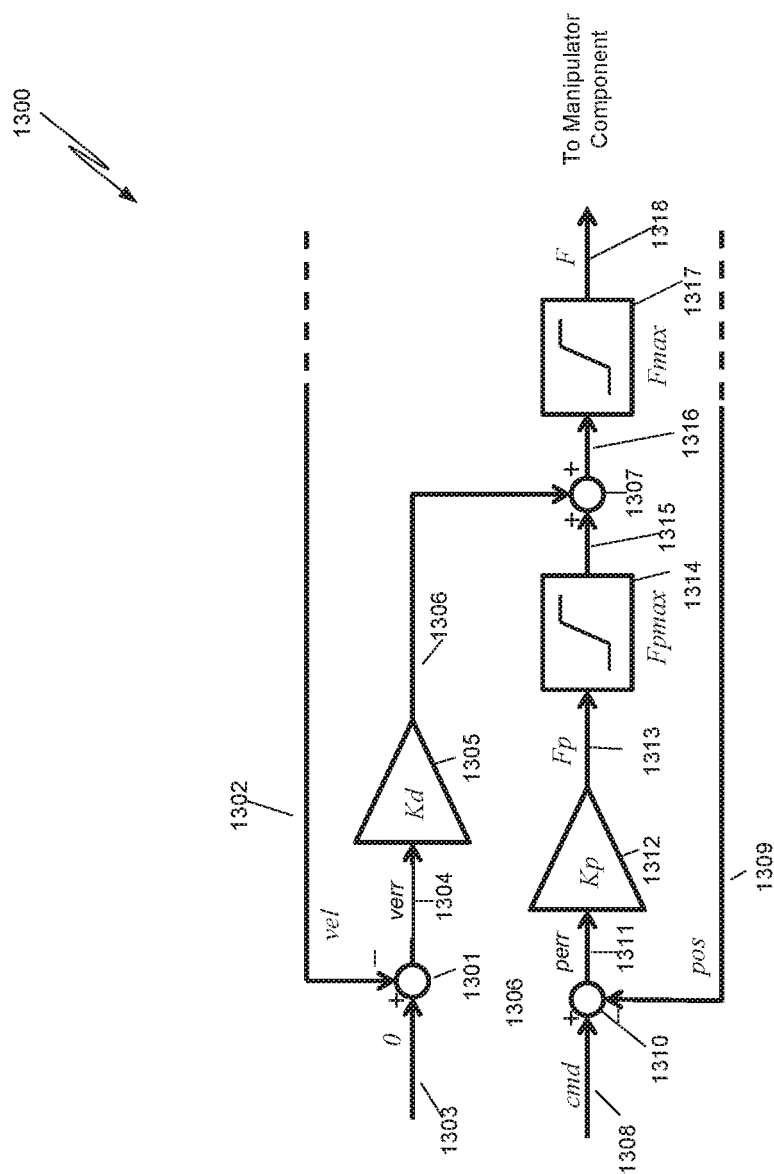
FIG. 13 is a representation of a position drift control loop that is implemented within a servo-loop of a controller.

FIGS. 11 and 12 are alternative implementations of a state machine in controller 690 that is used to perform methods 900, 950, and 1000. FIG. 13 is a representation of a position drift control loop 1300 that is implemented within a servo-loop of controller 690 to perform the acts associated with the state machines of FIGS. 11 and 12. In the drawings, use of italics is the same as the use of bold in the text here, e.g., cmd in the drawings is the same as cmd herein. In general, a position drift control loop is a control loop configured in the controller so that a controlled part moves with constant speed and with reduced torque limits so that obstacles or user tapping of the controlled part are detected by a position tracking disturbance exceeding set limits. In this implementation a backdriveable drivetrain is utilized (the position drift control loop does not work with worm gears in the drive train), and the torque limits are set just above the intrinsic friction of the drivetrain. One way of implementing such a position drift control loop is by appropriately configuring the gains and torque limits in PD controller or a PID (proportional, integral, derivative) controller with cascaded saturations, as explained more completely below.

State machine 1100 includes a POSITION HOLD state 1101, an ADVANCE state 1102, and a DONE state 1103. State machine 1100 is enabled by DRAPE STEP EVENT DETECTED signal 1104.

As explained above, when a sterile surgical drape assembly 560 is first mounted on a patient side support system 610, a signal is sent to controller 690 that indicates the mounting. As various parts of patient side support system 610 are draped, signals are provided to controller 690, which indicate the status of the draping. Thus, when a manipulator component that is controlled by state machine 1100 is ready to be moved into or within the drape or moved to facilitate draping, controller 690 sends DRAPE STEP EVENT DETECTED signal 1104 to POSITION HOLD state 1101.

In POSITION HOLD state 1101, state machine 1100 provides a command signal cmd to drift control loop 1300. Command signal cmd is the latched (stored) position latchedpos of the manipulator component. Here, a manipulator component can be either a link of a patient side support system, a manipulator of a patient side support system, or some other component of the patient side support system. Thus, in POSITION HOLD state 1101, state machine 1100 commands the manipulator component to maintain latched position latchedpos.

While in In POSITION HOLD state 1101, the current position pos of the manipulator component is subtracted from the commanded position cmd to determine a position error of the manipulator component. If the position error is greater than a position error threshold thresh, state machine 1100 transitions form POSITION HOLD state 1101 to ADVANCE state 1102 only if the position error is greater than a position error threshold thresh for a predetermined time interval, i.e., longer than a minimum start time threshold, i.e., only if a position tracing disturbance occurred. In this example, the minimum start time threshold and the duration of the position error is determined in servo-loop cycles. The duration of the position error is a number consecutive of servo-loop cycles count that the position error exists. The minimum start time threshold is count_start, (a first time threshold) which is the minimum number of consecutive servo-loop cycles that the position error must be sensed.

In one aspect, position error threshold thresh and minimum start time threshold count_start are determined based on a combination of factors:

1) Mechanism performance: position error threshold thresh must be larger than the normal steady state position error of the controller. Position error threshold thresh combined with minimum start time threshold count_start are selected to allow discrimination between voluntary user actions from other disturbances present in the system; and
2) Usability aspects: position error threshold thresh and minimum start time threshold count_start should be as low as possible so that the system reacts to the shortest/ most gentle voluntary tap by a user.

In general, this requires that the mechanism performance be very good (e.g. through a precise compensation of the gravity and friction forces that may result in large steady state tracking errors), to make the mechanism behavior responsive to a tap of the user.

In practical terms, in one aspect the following parameters were used:

thresh=−0.04 mm count_start=4 (corresponding to 3 ms)

Thus, state machine 1100 transitions form POSITION HOLD state 1101 to ADVANCE state 1102 if:

pos−cmd>thresh

AND count>count_start

When state machine 1100 transitions from POSITION HOLD state 1101 to ADVANCE state 1102, a message is also sent to a graphic user interface denoting the state change of the manipulator component. This implementation applies to a manipulator component that is backdriveable and for which tapping of the manipulator component can be sensed via a position error. Alternatively, direct force sensing on the manipulator component could be used to detect the tapping.

In ADVANCE state 1102, state machine 1100 provides a command signal cmd to drift control loop 1300. The command signal cmd is a desired position goal of the manipulator component. In one aspect, position goal is determined as the insertion assembly position that allows full unfolding of the drape sleeve while leaving a bit of slack for the user to click in the sterile adapter (in one aspect, position goal is a 390 mm from the home position, but position goal may vary with different drape designs and insertion assembly stroke). Thus, in ADVANCE state 1102, controller 690 automatically moves the manipulator component.

State machine 1100 remains in ADVANCE state 1102 until two conditions are met. First, a velocity vel of the manipulator component must be less than a predetermined minimum velocity vel_min. Second, the velocity vel of the manipulator component must be less than predetermined minimum velocity vel_min for a predetermined time interval, i.e., longer than a minimum stop time threshold. In this example, the minimum stop threshold also is determined in servo-loop cycles. The time duration of the velocity vel of the manipulator component being less than a predetermined minimum velocity vel_min is a number consecutive of servo-loop cycles count. The minimum stop time threshold is count_stop (a second time threshold), which is the minimum number of consecutive servo-loop cycles that velocity vel of the manipulator component is less than a predetermined minimum velocity vel_min.

In one aspect, the following values of predetermined minimum velocity vel_min and minimum stop time threshold is count_stop are used:

vel_min=0.1 mm/s count_stop=1 (corresponding to 0.75 ms).

Within the limits discussed above for position error threshold thresh and minimum start time threshold count_start, predetermined minimum velocity vel_min and minimum stop time threshold is count_stop are set to be more responsive than position error threshold thresh and minimum start time threshold count_start, which are necessary to get the drift started. This is necessary assure that the motion of the manipulator component stops immediately if the drape is caught in the patient side support system or in presence of other obstacles. An accidental stop is preferable over loss of sterility.

Thus, state machine 1100 transitions from ADVANCE state 1102 back to POSITION HOLD state 1101 if:

vel<vel_min

AND count>count_stop

As state machine 1100 transitions from ADVANCE state 1102 back to POSITION HOLD state 1101, state machine 1100 latches the current position of the manipulator component as latched (stored) position latchedpos. A message is also sent to the graphic user interface denoting the state change of the manipulator component.

Again, stopping the advancement of the manipulator component in this implementation applies to a manipulator component that is backdriveable and for which stopping of the manipulator component can be sensed via a velocity. Alternatively, direct force sensing on the manipulator component could be used to detect the stopping of the manipulator component.

State machine 1100 remains in POSITION HOLD state 1101 until either the two conditions for transition to ADVANCE state 1102 are met, or one of the two conditions for transition to DONE state 1103 are met. First, in one aspect, if the sterile adapter assembly has been mounted on the surgical instrument manipulator assembly so that a signal Sterile Adapter ON is provided by the patient side support system to controller 690, state machine 1100 transitions from POSITION HOLD state 1101 to DONE state 1103. Alternatively, if position pos of the manipulator component is a final position final_pos, state machine 1100 transitions from POSITION HOLD state 1101 to DONE state 1103. In one aspect, final position final_pos is a threshold that allows a range about position goal. For example, final position final_pos is determined as a range about which the drape is sufficiently unfolded and not stretched too much so to allow sterile adapter installation.

Thus, state machine 1100 transitions from POSITION HOLD state 1101 to DONE state 1103 if:

Sterile Adapter ON

OR pos=final_pos

In this example, a state machine for a single joint or insertion assembly has been considered. However, these conditions can be extended, in a vector sense, to a number of joints of a mechanism or to multiple mechanisms controlled through a distributed computing architecture.

State machine 1200 includes a READY state 1201, an ADVANCE state 1202, a POSITION HOLD state 1203, and a DONE state 1204. State machine 1200 is enabled by DRAPE STEP EVENT DETECTED signal 1205. In the following discussion, a parameter with the same name as a parameter discussed with respect to state machine 1100 is the same parameter.

As explained above, when a sterile surgical drape is first mounted on a patient side support system, a signal is sent to a controller that indicates the mounting. As various parts of patient side support system are draped, signals are provided to the controller, which indicate the status of the draping. Thus, when a manipulator component that controlled by state machine 1200 is ready to be moved into or within the drape or moved to facilitate draping, controller 690 sends DRAPE STEP EVENT DETECTED signal 1205 to READY state 1201.

In READY state 1201, state machine 1200 provides a command signal cmd to drift control loop 1300. Command signal cmd is the latched (stored) position latchedpos of the manipulator component. In READY state 1201, state machine 1200 commands the manipulator component to maintain latched position latchedpos.

While in READY state 1201, the current position pos of the manipulator component is subtracted by controller 690 from the commanded position cmd to determine a position error of the manipulator component. If the position error is greater than a position error threshold thresh, state machine 1200 transitions form READY state 1201 to ADVANCE state 1202 only if the position error is greater than a position error threshold thresh for a predetermined time interval, i.e., longer than a minimum time threshold, i.e., only if a position tracking disturbance occurred. In this example, the minimum time threshold and the duration of the position error is determined in servo-loop cycles. The duration of the position error is a number consecutive of servo-loop cycles count that the position error exists. The minimum start time threshold is count_start, which is the minimum number of consecutive servo-loop cycles that the position error must be sensed.

Thus, state machine 1200 transitions form READY state 1201 to ADVANCE state 1202 if:

pos−cmd>thresh
 AND
count>count_start

When state machine 1200 transitions from READY state 1201 to ADVANCE state 1202, a message is also sent to a graphic user interface denoting the state change of the manipulator component. This message is the same as the one that is sent when transitioning to POSITION HOLD state 1203. This implementation applies to a manipulator component that is backdriveable and for which tapping of the manipulator component can be sensed via a position error. Alternatively, direct force sensing on the manipulator component could be used to detect the tapping.

In ADVANCE state 1202, state machine 1200 provides a command signal cmd to drift control loop 1300. The command signal cmd is desired position goal of the manipulator component. Thus, in ADVANCE state 1202, controller 690 automatically moves the manipulator component.

State machine 1200 remains in ADVANCE state 1202 until two conditions are met. First, the velocity vel of the manipulator component must be less than a predetermined minimum velocity vel_min. Second, the velocity vel of the manipulator component must be less than predetermined minimum velocity vel_min for a predetermined time interval, i.e., longer than a minimum stop time threshold. In this example, the minimum stop threshold also is determined in servo-loop cycles. The time duration of the velocity vel of the manipulator component being less than a predetermined minimum velocity vel_min is a number consecutive of servo-loop cycles count. The minimum stop time threshold is count_stop, which is the minimum number of consecutive servo-loop cycles that the velocity vel of the manipulator component must be less than a predetermined minimum velocity vel_min.

Thus, state machine 1200 transitions from ADVANCE state 1202 to POSITION HOLD state 1203 if:

vel<vel_min
 AND
count>count_stop

As state machine 1200 transitions from ADVANCE state 1202 back to POSITION HOLD state 1203, state machine 1200 latches the current position of the manipulator component as latched (stored) position latchedpos. A message is also sent to the graphic user interface denoting the state change of the manipulator component.

Again, stopping the advancement of the manipulator component in this implementation applies to a manipulator component that is backdriveable and for which stopping the manipulator component can be sensed via a velocity. Alternatively, direct force sensing on the manipulator component could be used to detect the advancement of the manipulator component.

In POSITION HOLD state 1203, state machine 1200 provides a command signal cmd to drift control loop 1300. Command signal cmd is the latched (stored) position latchedpos of the manipulator component. In POSITION HOLD state 1203, state machine 1200 commands the manipulator component to maintain latched position latchedpos.

State machine 1200 remains in POSITION HOLD state 1203 until a condition to transition to READY state 1201 is met, or one the two conditions for transition to DONE state 1204 are met. READY state 1201 is a way to enforce a minimum time spent holding a position of the manipulator component. This improves the stop performance, because otherwise the momentum of the manipulator component as the component comes to rest might introduce a position error that is large enough to cause a transition from POSITION HOLD state 1101 to ADVANCE state 1102 in state machine 1100.

Thus, state machine 1200 stays in POSITION HOLD state 1203 a predetermined amount of time and then transitions to READY state 1201 if neither of the conditions for transition to DONE state 1204 are met. In this example, the amount of time count spent in POSITION HOLD state 1203 is the number of servo-loop cycles since the transition to POSITION HOLD state 1203. If time count is larger than the predetermined minimum ready count time count_ready, (a third time threshold) expressed in servo-loop cycles, state machine 1200 transitions from POSITION HOLD state 1203 to READY state 1201.

Because of the way the drift of the manipulator component is implemented, the actual position of the manipulator component lags behind the commanded position, and not allowing for enough time through subsequent activations causes discontinuities in the forces felt by the user. Staying in POSITION HOLD state 1203 a predetermined amount of time essentially makes sure that the drift can be re-enabled without side effects, and it's almost invisible to the user since predetermined minimum ready count time count_ready is normally below the time it takes the user to inspect the drape and restart the drift. In one aspect, predetermined minimum ready count time count_ready is set to 667 counts (0.5 sec with a servo period of 0.75 ms)

Thus, state machine 1200 transitions from POSITION HOLD state 1203 to READY state 1201 if:

count>count_ready

In one aspect, if the sterile adapter assembly has been mounted on the surgical instrument manipulator assembly so that a signal Sterile Adapter ON is provided by the patient side support system to controller 690, state machine 1200 transitions from POSITION HOLD state 1203 to DONE state 1204. Alternatively, if position pos of the manipulator component is a final position final_pos, state machine 1200 transitions from POSITION HOLD state 1203 to DONE state 1204.

Thus, state machine 1200 transitions from POSITION HOLD state 1203 to DONE state 1204 if.

Sterile Adapter ON
 OR
pos=final_pos

In this example, a state machine for a single joint or insertion assembly has been considered. However, these conditions can be extended, in a vector sense, to a number of joints of a mechanism or to multiple mechanisms controlled through a distributed computing architecture.

As indicated above, FIG. 13 is a representation of a drift control loop 1300 that is implemented within a servo-loop of controller 690. In this example, drift control loop 1300 is a feedback proportional differential (PD) controller with cascaded saturations. The advancement trajectory for the manipulator component in the ADVANCE state of state machines 1100 and 1200 could be determined as, for example, a polynomial or trapezoidal trajectory with a real-time trajectory planner. However, this complexity is avoided with the structure depicted in FIG. 13.

An inverting terminal of a first summing junction 1301 receives a velocity signal vel, which represents the velocity of the manipulator component, on a velocity line 1302. A stationary velocity signal 0, which represents the stationary velocity of the manipulator component, on line 1303 is provided to a plus terminal of first summing junction 1301. A velocity error line 1304 provides a velocity error signal verr from the output terminal of first summing junction 1301 to an input terminal of a derivative gain 1305. Derivative gain 1305 multiplies the signal on the input terminal by constant Kd. The derivative component of the controller force output signal from derivative gain 1305 is input on a first plus terminal of a third summing junction 1307.

An inverting terminal of a second summing junction 1310 receives a position signal pos on a position line 1309. Position signal pos represents the position of the manipulator component. A commanded position signal cmd, which represents a desired position—the latched position or the goal position—of the manipulator component, on line 1308 is provided to a plus terminal of second summing junction 1310. A position error line 1311 provides a position error signal perr from the output terminal of second summing junction 1310 to an input terminal of a proportional gain 1312, which in some embodiments may be implemented with an amplifier. Proportional gain 1312 multiplies the input signal by constant Kp. This converts the position-based position error to a position-based force error signal Fp. Output signal Fp from proportional gain 1312 on line 1313 is connected to an input of a first saturation block 1314.

Saturation block 1314 implements the following functionality:

| | Output signal |
|---|---|
| Input signal Fp within a range between - Fpmax and Fpmax | Fp |
| Input signal Fp greater than Fpmax in magnitude (|Fp| > Fpmax) | ±Fpmax |

Constants Kd and Fpmax are selected to determine the drift velocity of the manipulator component. The output signal from saturation block 1314 on line 1315 is input to a second plus terminal of third summing junction 1307.

Third summing junction 1307 adds the signal on line 1306 to the signal on line 1315 and the result is output on line 1316 to an input terminal of a second saturation block 1317. Saturation block 1317 implements the following functionality:

| | Output signal |
|---|---|
| Input signal within a range between - Fmax and Fmax | Expression (1) below |
| Input signal greater than Fmax in magnitude | Fmax |

Here, force Fmax is the maximum force that can be applied on the manipulator component. The output signal from saturation block 1317 is a force signal F that is sent to the manipulator component. Thus, in this implementation, output force signal F of loop 1300 is:

$$F=\text{sat}\{\text{sat}\{Kp(\text{cmd}-\text{pos}), F\text{pmax}\}+Kd(0-\text{vel}), F\text{max}\} \quad (1)$$

where
  Fmax=sat{sat{Fp−Kd*verr}, Fpmax}
  sat {Kp(cmd−pos), Fpmax} is interpreted as:
    Fpmax is the saturation limit
    Input signal is Kp(cmd−pos)
      Output signal is:
      Kp*(cmd−pos) when |Kp*(cmd−pos)|<Fpmax
      Fpmax when Kp*(cmd−pos)>Fpmax
      −Fpmax when Kp*(cmd−pos)<−Fpmax
Drift velocity vdrift of the manipulator component due to force F is:

$$v\text{drift}=F p\text{max}/Kd$$

Control loop 1300 has the advantage of simultaneously making the manipulator component move at a controlled speed and of determining how compliant the motion is through parameter Fmax.

In the above description, the manipulator component has been described as a link or a surgical instrument manipulator. However, when it is said that a force or signal is sent to the manipulator component, it should be understood that the force or signal is sent to a component which causes the manipulator component to move, e.g., an actively controlled joint for the link, or a motor of an insertion assembly to which the surgical instrument manipulator assembly is attached for the surgical instrument manipulator assembly. Use of an actively controlled joint to control motion of a link is known and so is not considered in further detail. Similarly, use of an insertion assembly to move a surgical instrument manipulator assembly is known, and so also is not considered in further detail.

In some of the above examples, the terms "proximal" or "proximally" are used in a general way to describe an object or element which is closer to a manipulator arm base along a kinematic chain of system movement or farther away from a remote center of motion (or a surgical site) along the kinematic chain of system movement. Similarly, the terms "distal" or "distally" are used in a general way to describe an object or element which is farther away from the manipulator arm base along the kinematic chain of system movement or closer to the remote center of motion (or a surgical site) along the kinematic chain of system movement.

As used herein, "first," "second," "third," "fourth," etc. are adjectives used to distinguish between different components or elements. Thus, "first," "second," "third," "fourth," etc. are not intended to imply any ordering of the components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below"

or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

The various controllers described herein can be implemented by software executing on a processor, hardware, firmware, or any combination of the three. When the controllers are implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the various controllers, as described herein, may be performed by one unit, or divided up among different components, each of which may be implemented in turn by any combination of hardware, software that is executed on a processor, and firmware. When divided up among different components, the components may be centralized in one location or distributed across the system for distributed processing purposes. The execution of the various controllers results in methods that perform the processes described above for the various controllers.

A processor is coupled to a memory containing instructions executed by the processor. This could be accomplished within a computer system, or alternatively via a connection to another computer via modems and analog lines, or digital interfaces and a digital carrier line, or via connections using any of the protocols described above. In view of this disclosure, instructions used in any part of or all of the processes described herein can be implemented in a wide variety of computer system configurations using an operating system and computer programming language of interest to the user.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives, and other physical storage mediums.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

What is claimed is:

1. A system comprising:
   a moveable component; and
   a controller coupled to the moveable component;
   wherein the controller is configured to:
      hold the moveable component at a first position;
      detect that the moveable component has been moved from the first position, at which the moveable component was being held, for at least a first predetermined duration of time, due to a disturbance;
      in response to the detection that the moveable component has been moved from the first position for at least the first predetermined duration of time, move the moveable component according to a first motion;
      continue to move the moveable component according to the first motion until a stop condition is detected, even if the disturbance ends before the stop condition is detected; and
      in response to a detection of the stop condition, hold the moveable component at a second position.

2. The system of claim 1, wherein:
   the system is a surgical system; and
   the first motion moves the moveable component into a portion of a surgical drape.

3. The system of claim 1, wherein the moveable component comprises a link of an instrument manipulator.

4. The system of claim 1, wherein the first motion is in a direction of the disturbance.

5. The system of claim 1, wherein to detect that the moveable component has been moved from the first position, the controller is configured to detect that the moveable component has been moved from the first position by more than a threshold amount for at least the first predetermined duration of time.

6. The system of claim 1, wherein to detect that the moveable component has been moved from the first position, the controller is configured to detect a pattern of two or more changes in a position of the moveable component from the first position.

7. The system of claim 1, wherein to detect that the moveable component has been moved from the first position, the controller is configured to detect one or more external taps on the moveable component.

8. The system of claim 1, wherein the stop condition comprises the moveable component reaching the second position or the moveable component moving a predetermined distance.

9. The system of claim 1, wherein the stop condition comprises a speed of the moveable component remaining below a threshold speed for a second predetermined duration of time.

10. The system of claim 1, wherein the controller is further configured to:

detect that the moveable component has been moved from the second position due to a second disturbance; and in response to the detection that the moveable component has been moved from the second position, move the moveable component according to a second motion.

11. The system of claim 1, wherein:
the first motion is included in a sequence of motions of the moveable component; and
each motion in the sequence of motions is performed in response to a corresponding movement of the moveable component from a corresponding position.

12. A method for controlling a moveable component, the method comprising:
holding, by a controller, the moveable component at a first position;
detecting, by the controller, that the moveable component has been moved from the first position at which the moveable component was being held, for at least a first predetermined duration of time, due to a disturbance;
moving, by the controller in response to detecting that the moveable component has been moved from the first position for at least the first predetermined duration of time, the moveable component according to a first motion;
continuing to move the moveable component, by the controller, according to the first motion until a stop condition is detected, even if the disturbance ends before the stop condition is detected; and
holding, by the controller in response to a detection of the stop condition, the moveable component at a second position.

13. The method of claim 12, wherein the first motion is in a direction of the disturbance.

14. The method of claim 12, wherein detecting that the moveable component has been moved from the first position comprises:
detecting that the moveable component has moved from the first position by more than a threshold amount for at least the first predetermined duration of time; or
detecting a pattern of two or more changes in a position of the moveable component from the first position; or
detecting one or more external taps on the moveable component.

15. The method of claim 12, wherein the stop condition comprises:
the moveable component reaching the second position; or
the moveable component moving a predetermined distance; or
a speed of the moveable component remaining below a threshold speed for a second predetermined duration of time.

16. The method of claim 12, further comprising:
detecting, by the controller, that the moveable component has been moved from the second position due to a second disturbance; and
moving, by the controller and in response to detecting that the moveable component has been moved from the second position, the moveable component according to a second motion.

17. A non-transitory computer-readable medium storing instructions for controlling operation of one or more hardware processors to perform a method comprising:
holding a moveable component at a first position;
detecting that the moveable component has been moved from the first position at which the moveable component was being held, for at least a first predetermined duration of time, due to a disturbance;
in response to detecting that the moveable component has been moved from the first position for at least the first predetermined duration of time, moving the moveable component according to a first motion;
continuing to move the moveable component according to the first motion until a stop condition is detected, even if the disturbance ends before the stop condition is detected; and
in response to a detection of the stop condition, holding the moveable component at a second position.

18. The non-transitory computer-readable medium of claim 17, wherein the first motion is in a direction of the disturbance.

19. The non-transitory computer-readable medium of claim 17, wherein detecting that the moveable component has been moved from the first position comprises:
detecting that the moveable component has moved from the first position by more than a threshold amount for at least the first predetermined duration of time; or
detecting a pattern of two or more changes in a position of the moveable component from the first position; or
detecting one or more external taps on the moveable component.

20. The non-transitory computer-readable medium of claim 17, wherein the stop condition comprises:
the moveable component reaching the second position; or
the moveable component moving a predetermined distance; or
a speed of the moveable component remaining below a threshold speed for a second predetermined duration of time.

* * * * *

UNITED STATES PATENT AND TRADEMARK OFFICE
CERTIFICATE OF CORRECTION

| | |
|---|---|
| PATENT NO. | : 11,766,301 B2 |
| APPLICATION NO. | : 17/236868 |
| DATED | : September 26, 2023 |
| INVENTOR(S) | : Nicola Diolaiti et al. |

It is certified that error appears in the above-identified patent and that said Letters Patent is hereby corrected as shown below:

On the Title Page

(63) Related U.S. Application Data:
Please delete "Continuation of application No. 16/317,334, filed as application No. PCT/US2017/032930 on May 16, 2017, now Pat. No. 11,020,191." and insert --Continuation of application No. 16/317,334, filed on Jan. 11, 2019, now Pat. No. 11,020,191, which is a 371 of application No. PCT/US2017/032930, filed on May 16, 2017.--.

Signed and Sealed this
Twenty-fourth Day of October, 2023

Katherine Kelly Vidal
*Director of the United States Patent and Trademark Office*